(12) United States Patent
Du et al.

(10) Patent No.: US 7,098,340 B2
(45) Date of Patent: Aug. 29, 2006

(54) BENZYL SULFONAMIDE DERIVATIVES

(75) Inventors: Daniel Y. Du, Milan, MI (US); Martin James Procter, Bicester (GB); Matthew Colin Thor Fyfe, Witney (GB); Vilasben Kanji Shah, Hall Green (GB); Geoffrey Martyn Williams, Oxford (GB); Karen Lesley Schofield, Oxford (GB)

(73) Assignee: Warner Lambert Company LLC, Morris Plains, NJ (US)

( * ) Notice: Subject to any disclaimer, the term of this patent is extended or adjusted under 35 U.S.C. 154(b) by 273 days.

(21) Appl. No.: 10/824,456

(22) Filed: Apr. 14, 2004

(65) Prior Publication Data

US 2005/0137228 A1    Jun. 23, 2005

Related U.S. Application Data

(60) Provisional application No. 60/470,569, filed on May 14, 2003.

(51) Int. Cl.
*C07D 215/16*    (2006.01)

(52) U.S. Cl. ...................................................... 546/158

(58) Field of Classification Search ................. 546/158
See application file for complete search history.

(56) References Cited

U.S. PATENT DOCUMENTS 5,616,712 A * 4/1997 Teng et al. .................. 546/158
6,017,924 A   1/2000 Edwards et al.

FOREIGN PATENT DOCUMENTS

| WO | WO 96/36609 | 11/1996 |
| WO | WO 96/37490 | 11/1996 |
| WO | WO 01/16108 | 3/2001 |
| WO | WO 01/16133 | 3/2001 |
| WO | WO 01/16139 | 3/2001 |
| WO | WO 01/49673 A2 | 7/2001 |
| WO | WO 02/16130 A1 | 2/2002 |

* cited by examiner

*Primary Examiner*—D. Margaret Seaman
(74) *Attorney, Agent, or Firm*—J. Michael Dixon; Charles W. Ashbrook

(57) ABSTRACT

The present invention is directed to a new class of 6-benzylsulfonamido-quinoline/chromene derivatives, to their use as androgen antagonists, and to formulations containing these androgen antagonists.

11 Claims, No Drawings

BENZYL SULFONAMIDE DERIVATIVES

CROSS-REFERENCE TO RELATED APPLICATIONS

This application claims the benefit of U.S. Provisional Application Ser. No. 60/470,569 filed May 14, 2003.

FIELD OF THE INVENTION

The present invention is directed to a new class of quinolin-2-ones and chromen-2-ones (hereinafter "quinolines and chromenes"), to their use as androgen receptor antagonists, to medicinals containing these compounds and to their use to alleviate conditions associated with inappropriate activation of the androgen receptor.

BACKGROUND OF THE INVENTION

The androgen receptor (AR) is a member of the steroid receptor (SR) family of transcriptional regulatory proteins that transduces the signaling information conveyed by androgens. Upon androgen binding, the androgen receptor is released from the repressive effects of an Hsp 90-based regulatory complex, allowing the receptor to either activate or inhibit transcription of target genes in a hormone-dependent manner. In addition to the role the androgen receptor plays in male sex determination, its activation plays a critical role in the development and progression of benign prostate hyperplasia, prostate cancer, seborrhea, acne, premenstrual syndrome, lung cancer, ovarian polycyclic syndrome, hirsutism, and hair loss. Thus, the androgen receptor is an important target in multiple areas of drug discovery.

U.S. Pat. No. 6,017,924 discloses a class of non-steroidal compounds, pyridinoquinolines that have affinity for the androgen receptor. The '924 patent describes these compounds as being agonists, partial agonists, antagonists, and partial antagonists, etc. The '924 patent provides no guidance on how to achieve a specific biological effect (i.e. agonist versus antagonist). Agonists have the ability to masculinize females, whereas antagonists feminize males. Such side effects limit the potential applicability of androgen therapy.

PCT applications WO 01/16133 and WO 01/16139 also disclose non-steroidal compounds that have affinity for the androgen receptor. Examples of such structures include pyrazinoquinolines, oxazinoquinolines, and pyridinoquinolines. The PCT application does not disclose any 6-benzyl-sulfonamido-quinolin-2-ones or 6-benzylsulfonamido-chromen-2-ones.

PCT application WO 01/16108 discloses non-steroidal compounds having affinity for the androgen receptor. Like the '924 patent described above, the compounds are described as having both agonist and antagonist effects. Some of the compounds of the PCT application are quinolin-2-one derivatives. The PCT application does not disclose any 6-benzylsulfonamido-quinolin-2-ones or 6-benzylsulfonamido-chromen-2-ones.

While the prior art describes compounds having affinity for the androgen receptor, it does not describe how to achieve selectivity with respect to this affinity (i.e. agonist or antagonist). The physiological impact of this affinity is often an undesirable side effect, depending upon the gender of the patient. Thus a need exists in the art for androgen receptor antagonists.

SUMMARY OF THE INVENTION

In accordance with the present invention, a new class of androgen antagonists have been discovered. These compounds may be represented by Formula I depicted below:

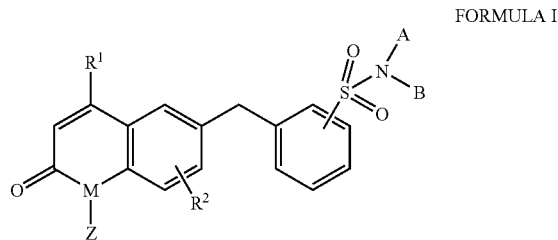

FORMULA I in which:
a. M is NZ or O;
b. Z is represented by H or $C_1$–$C_4$ alkyl;
c. $R^1$ is represented by hydrogen, ($C_1$–$C_2$)alkyl, optionally substituted with one or more halogens, or ($C_1$–$C_2$) alkoxy, optionally substituted with 1 or more halogens;
d. $R^2$ is absent, or may represent up to 2 substituents selected from the group consisting of halogen, nitrile, hydroxy, ($C_1$–$C_4$)alkyl, ($C_2$–$C_4$)alkenyl, ($C_2$–$C_4$)alkynyl, ($C_1$–$C_4$)alkoxy, ($C_1$–$C_2$)alkyl substituted with 1 or more halogens, ($C_1$–$C_2$)alkoxy substituted with one or more halogens, $SR^4$, and $NR^4R^5$;
e. $R^4$ is represented by hydrogen, ($C_1$–$C_4$)alkyl, optionally substituted phenyl, or optionally substituted benzyl;
f. $R^5$ is represented by hydrogen, ($C_1$–$C_4$)alkyl, optionally substituted phenyl, optionally substituted benzyl, optionally substituted heteroaryl, or optionally substituted heterocyclic;
g. A and B are each independently represented by a substituent selected from the group consisting of hydrogen, ($C_1$–$C_6$)alkyl optionally substituted with one or more halogens, ($C_2$–$C_6$)alkenyl, ($C_2$–$C_6$)alkynyl, ($C_1$–$C_4$)alkanol, optionally substituted ($C_3$–$C_8$)cycloalkyl, optionally substituted ($C_5$–$C_8$)cycloalkenyl, optionally substituted phenyl, optionally substituted cycloalkylphenyl, optionally substituted heterocyclic, optionally substituted heteroaryl, ($C_1$–$C_6$)alkyl$R^6$, —$(CH_2)_m$—$R^7$—Y—[—$CH_2$]$_n$—X—$R^8$, —$(CH_2)_q$ $CHX^1X^2$;
h. $R^6$ is represented by a substituent selected from the group consisting of nitrile, OH, optionally substituted phenyl, optionally substituted cyloalkylphenyl, optionally substituted heterocyclic, optionally substituted heteroaryl, optionally substituted ($C_3$–$C_8$)cycloalkyl, optionally substituted ($C_5$–$C_8$)cycloalkenyl, $SR^4$, $NR^4R^5$,
i. m is an integer selected from 0, 1, 2, 3, or 4;
j. $R^7$ is absent, or is represented by a substituent selected from the group consisting of optionally substituted ($C_3$–$C_8$)cycloalkyl, optionally substituted ($C_5$–$C_8$)cycloalkenyl, optionally substituted heteroaryl, optionally substituted heterocyclic, and optionally substituted phenyl,
k. $R^8$ is absent, or is represented by a substituent selected from the group consisting of ($C_1$–$C_6$)alkyl, optionally substituted ($C_3$–$C_8$)cycloalkyl, optionally substituted ($C_5$–$C_8$)cycloalkenyl, optionally substituted heteroaryl, optionally substituted heterocyclic, optionally substituted phenyl, and optionally substituted cycloalkylphenyl;

l. Y is absent, or is represented by O, C(O), C(O)O, $CH_2C(O)O$, OH, SH, S, or $NR^4$;

m. n is represented by an integer selected from 0, 1, 2, 3, or 4;

n. X is absent, or is represented by O, C(O), C(O)O, $-CH_2C(O)O$, OH, SH, S, or $NR^4$;

o. q is represented by an integer selected from 0, 1, 2, 3, or 4;

p. $X^1$ is represented by a substituent selected from the group consisting of hydroxy, nitrile, $CH_2C(O)OR^4$, $C(O)OR^4$, $(C_1-C_6)$alkyl, $(C_2-C_6)$alkenyl, $(C_2-C_6)$alkynyl, $(C_1-C_4)$alkanol, $(C_1-C_2)$alkyl substituted with 1 or more halogens, $(C_1-C_2)$alkoxy substituted with one or more halogens, optionally substituted $(C_3-C_8)$ cycloalkyl, optionally substituted $(C_5-C_8)$cycloalkenyl, optionally substituted heteroaryl, optionally substituted heterocyclic, optionally substituted phenyl, and optionally substituted cycloalkylphenyl;

q. $X^2$ is represented by a substituent selected from the group consisting of hydroxy, nitrile, $CH_2C(O)OR^4$, $C(O)OR^4$, $(C_1-C_6)$alkyl, $(C_2-C_6)$alkenyl, $(C_2-C_6)$alkynyl, $(C_1-C_4)$alkanol, $(C_1-C_2)$alkyl substituted with 1 or more halogens, $(C_1-C_2)$alkoxy substituted with one or more halogens, optionally substituted $(C_3-C_8)$ cycloalkyl, optionally substituted $(C_5-C_8)$cycloalkenyl, optionally substituted heteroaryl, optionally substituted heterocyclic, optionally substituted phenyl, and optionally substituted cycloalkylphenyl, and;

r. the pharmaceutically acceptable salts, solvates, and prodrugs thereof.

The compounds of Formula I are androgen receptor antagonists. The compounds will inhibit, or decrease, activation of the androgen receptor by androgens. The compounds can be used to treat, or alleviate, conditions associated with inappropriate activation of the androgen receptor. Examples of such conditions include, but are not limited to, acne, excess seborrhea secretion, alopecia, prostate cancer, hirsutism, etc.

The invention is also directed to pharmaceutical compositions containing at least one of the compounds of Formula I, in an amount effective to decrease activation of the androgen receptor. In a further embodiment, the invention is directed to an article of manufacture containing a compound of Formula I, packaged for retail distribution, in association with instructions advising the consumer on how to use the compound to alleviate a condition associated with inappropriate activation of the androgen receptor. An additional embodiment is directed to the use of a compound of Formula I as a diagnostic agent to detect inappropriate activation of the androgen receptor.

In a further embodiment, the compounds of Formula I are used topically to induce and/or stimulate hair growth and/or to slow down hair loss. The compounds may also be used topically in the treatment of hyperseborrhoea and/or of acne.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "$C_1-C_4$ alkyl" and "lower alkyl" refers to a branched or straight chained alkyl group containing from 1 to 4 carbon atoms, such as methyl, ethyl, n-propyl, isopropyl, n-butyl, isobutyl, etc.

b. "$C_1-C_6$ alkyl" refers to a branched or straight chained alkyl group containing from 1 to 6 carbon atoms, such as methyl, ethyl, n-propyl, isopropyl, n-butyl, isobutyl, n-pentyl, isopentyl, n-hexyl, etc.

c. "halogen" refers to a chlorine, fluorine or bromine atom.

d. "$C_1-C_2$ alkyl substituted with one or more halogen atoms" refers to a straight chained alkyl group containing 1 or 2 carbon atoms, i.e. methyl or ethyl, in which at least one hydrogen atom is replaced with a halogen. Examples include chloromethyl, difluoromethyl, trifluoromethyl, etc.

e. "lower alkoxy group" and "$C_1-C_4$ alkoxy" refers to a straight or branched chain alkoxy group containing from 1 to 4 carbon atoms, such as methoxy, ethoxy, n-propoxy, isopropoxy, n-butoxy, isobutoxy, etc.

f. "$C_2-C_4$ alkenyl" refers to a straight-chain or branched-chain hydrocarbon radical containing from 2 to 4 carbon atoms and 1, or more, carbon-carbon double bonds. Examples of alkenyl radicals include ethenyl, propenyl, 1,4-butadienyl and the like.

g. "$C_2-C_6$ alkenyl" refers to a straight-chain or branched-chain hydrocarbon radical containing from 2 to 6 carbon atoms and 1, or more, carbon-carbon double bonds. Examples of alkenyl radicals include ethenyl, propenyl, 1,4-butadienyl, pentenyl, hexenyl and the like.

h. "$C_2-C_4$ alkynyl" refers to a straight-chain or branched-chain hydrocarbon radical containing from 2 to 4 carbon atoms and having 1 or more carbon-carbon triple bonds. Examples of alkynyl radicals include ethynyl, propynyl, butynyl and the like.

i. "$C_2-C_6$ alkynyl" refers to a straight-chain or branched-chain hydrocarbon radical containing from 2 to 6 carbon atoms and having 1 or more carbon-carbon triple bonds. Examples of alkynyl radicals include ethynyl, propynyl, butynyl, pentynyl, hexynyl and the like.

j. "$(C_1-C_4)$alkylnitrile" refers to a straight-chain or branched chain alkyl group containing from 1 to 4 carbon atoms in which at least one hydrogen atom is replaced with a C≡N moiety.

k. "$(C_1-C_4)$alkanol" refers to a straight-chain or branched chained alkyl group containing from 1 to four carbon atoms group in which at least one hydrogen atom is replaced with a hydroxy function.

l. "optionally substituted phenyl" refers to a phenyl ($C_6H_5$) which is substituted with up to 3 substituents, each substituent is independently selected from the group consisting of halogen, nitrile, hydroxy, $(C_1-C_4)$ alkyl, $C_2-C_4$ alkenyl, $C_2-C_4$ alkynyl, $(C_1-C_4)$alkoxy, $(C_1-C_2)$alkyl substituted with one or more halogens, $(C_1-C_2)$alkoxy substituted with one or more halogens, $(C_1-C_4)$alkylnitrile, $(C_1-C_4)$alkanol, $SR^4$, and $NR^4R^5$. These substituents may be the same or different and may be located at any of the ortho, meta, or para positions.

m. "optionally substituted benzyl" refers to a benzyl $-CH_2-(C_6H_5)$ which is substituted with up to 3 substituents, each substituent is independently selected from the group consisting of halogen, nitrile, hydroxy, $(C_1–C_4)$alkyl, $C_2–C_4$ alkenyl, $C_2–C_4$ alkynyl, $(C_1–C_4)$alkoxy, $(C_1–C_2)$alkyl substituted with one or more halogens, $(C_1–C_2)$alkoxy substituted with one or more halogens, $(C_1–C_4)$alkylnitrile, $(C_1–C_4)$alkanol, $SR^4$, and $NR^4R^5$. These substituents may be the same or different and may be located at any of the ortho, meta, or para positions.

n. $(C_1–C_2)$alkoxy substituted with one or more halogen atoms refers to a straight chained alkoxy group containing 1 or 2 carbon atoms, ie, methoxy or ethoxy in which at least one hydrogen atom is replaced with a halogen.

o. "heteroaryl" refers to aromatic ring having one, or more, heteroatoms selected from oxygen, nitrogen and sulfur. More specifically, it refers to a 5- or 6-, membered ring containing 1, 2, or 3 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to quinolyl, isoquinolyl, benzofuryl, benzothienyl, pyrrolyl, furanyl, thienyl, imidazolyl, oxazolyl, indolyl, thiazolyl, pyrazolyl, pyridinyl, pyrimidinyl, purinyl, quinolinyl, and isoquinolinyl.

p. "optionally substituted heteroaryl" refers to a heteroaryl moiety as defined immediately above, in which up to 2 carbon atoms of the heteroaryl moiety may be substituted with a substituent, each substituent is independently selected from the group consisting of halogen, nitrile, hydroxy, $(C_1–C_4)$alkyl, $(C_2–C_4)$alkenyl, $(C_2–C_4)$alkynyl, $(C_1–C_4)$alkoxy, $(C_1–C_2)$alkyl substituted with one or more halogens, $(C_1–C_2)$alkoxy substituted with one or more halogens, $(C_1–C_4)$alkylnitrile, $(C_1–C_4)$alkanol, $SR^4$, and $NR^4R^5$. Further, any nitrogen atom of the heterocyclic ring may be substituted with a $C_1–C_4)$alkyl.

q. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example tetrahydroquinolyl, dihydrobenzofuryl and the like). Heterocyclics include: pyrrolidinyl, tetrahydrofuranyl, tetrahydrothiophenyl, piperidinyl, piperazinyl, azepane, azocane, morpholinyl, and tetraquinolinyl.

r. "optionally substituted heterocyclic" refers to a heterocyclic moiety as defined immediately above, in which up to 4 carbon atoms of the heterocycle moiety may be substituted with a substituent, each substituent is independently selected from the group consisting of halogen, nitrile, hydroxy, $(C_1–C_4)$alkyl, $C_2–C_4$ alkenyl, $C_2–C_4$ alkynyl, $(C_1–C_4)$alkoxy, $(C_1–C_2)$alkyl substituted with one or more halogens, $(C_1–C_2)$alkoxy substituted with 1 or more halogens, $(C_1–C_4)$alkylnitrile, $(C_1–C_4)$alkanol, oxo, $SR^4$, and $NR^4R^5$. Further, any nitrogen atom of the heterocyclic ring may be substituted with a $C_1–C_4)$alkyl.

s. "$C_3–C_8$ cycloalkyl" refers to a saturated or partially saturated monocyclic, bicyclic or tricyclic alkyl radical wherein each cyclic moiety has about 3 to about 8 carbon atoms. Examples of cyclcoalkyl radicals include cyclopropyl, cyclobutyl, cyclopentyl, cyclohexyl, norbornyl, and the like.

t. "optionally substituted "$C_3–C_8$ cycloalkyl" refers to a cycloalkyl moiety as defined immediately above in which up to 3 hydrogen atoms of the cycloalkyl moiety may be replaced with a substituent, each substituent is independently selected from the group consisting of halogen, nitrile, hydroxy, $(C_1–C_4)$alkyl, $C_2–C_4$ alkenyl, $C_2–C_4$ alkynyl , $(C_1–C_4)$alkoxy, $(C_1–C_2)$alkyl substituted with one or more halogens, $(C_1–C_2)$alkoxy substituted with one or more halogens, $(C_1–C_4)$alkylnitrile, $(C_1–C_4)$alkanol, $SR^4$, and $NR^4R^5$.

u. "$C_5–C_8$ cycloalkenyl" refers to a partially saturated monocyclic, bicyclic or tricyclic alkyl radical containing 1, or more, carbon-carbon double bonds, wherein each cyclic moiety has about 5 to about 8 carbon atoms. Examples of cycloalkenyl radicals include cyclopentenyl, cyclohexenyl, and the like v. "optionally substituted "$C_5–C_8$ cycloalkenyl" refers to a cycloalkenyl moiety as defined immediately above, in which up to 3 hydrogen atoms of the cycloalkyl moiety may be replaced with a substituent, each substituent is independently selected from the group consisting of halogen, nitrile, hydroxy, $(C_1–C_4)$alkyl, $C_2–C_4$ alkenyl, $C_2–C_4$ alkynyl , $(C_1–C_4)$alkoxy, $(C_1–C_2)$alkyl substituted with one or more halogens, $(C_1–C_2)$alkoxy substituted with one or more halogens, $(C_1–C_4)$alkylnitrile, $(C_1–C_4)$alkanol, $SR^4$, and $NR^4R^5$.

w. "cycloalkylphenyl" refers to a phenyl ring in which two carbon atoms of the phenyl ring complete a cyclobutyl, cyclopentyl, cyclohexyl, cycloheptyl, or cyclooctyl ring. Examples of such cycloalkylphenyl moieties include: indanyl, tetrahydronaphthyl, and the like.

x. "optionally substituted cycloalkylphenyl" refers to a cycloalkylphenyl moiety as described above, in which up to 3 hydrogen atoms of the cycloalkyl moiety may be replaced by a substituent, each substituent is independently selected from the group consisting of halogen, nitrile, hydroxy, $(C_1–C_4)$alkyl, $C_2–C_4$ alkenyl, $C_2–C_4$ alkynyl, $(C_1–C_4)$alkoxy, $(C_1–C_2)$alkyl substituted with one or more halogens, $(C_1–C_2)$alkoxy substituted with one or more halogens, $(C_1–C_4)$alkylnitrile, $(C_1–C_4)$alkanol, $SR^4$, and $NR^4R^5$.

y. "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.

z. "pharmaceutically acceptable salts" is intended to refer to either pharmaceutically acceptable acid addition salts" or "pharmaceutically acceptable basic addition salts" depending upon actual structure of the compound.

aa. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids.

Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

bb. "pharmaceutically acceptable basic addition salts" is intended to apply to any non-toxic organic or inorganic basic addition salts of the compounds represented by Formula I, or any of its intermediates.

Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

cc. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

dd. "compound of Formula I" "compounds of the invention" and "compounds" are used interchangeably throughout the application and should be treated as synonoms.

ee. "patient" refers to warm blooded animals such as, for example, guinea pigs, mice, rats, gerbils, cats, rabbits, dogs, monkeys, chimpanzees, and humans.

ff. "treat" refers to the ability of the compounds to either relieve, alleviate, or slow the progression of the patient's disease (or condition) or any tissue damage associated with the disease.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Some of the compounds of Formula I are based upon a 6-benzylquinolin-2-one nucleus. To further exemplify the invention this ring is depicted below along with its numbering system:

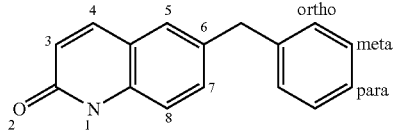

Ia

Position 1 of the quinoline nucleus contains a nitrogen atom. This nitrogen atom may be substituted with a lower alkyl group as described above. Position 6 of the quinoline ring will always be substituted with a benzyl moiety as depicted in FIG. Ia. Any of positions 3, 5, 7, or 8 of the quinoline nucleus may optionally be substituted with a substituent from the list described for $R^2$. Up to two of these positions may be substituted. Position 4 of the quinoline nucleus may optionally be substituted with one of the halogenated lower alkyl or alkoxy moieties described for $R^1$ above. Typically, Position 4 will be substituted with a trifluoromethyl function.

The benzyl moiety adjacent to position 6 will be further substituted with a sulfonamide moiety (—$SO_2$—NAB). The sulfonamide moiety may be attached to the ortho, meta, or para position of the benzyl ring (typically para).

The remaining compounds of Formula I are based upon a 6-benzyl-2-oxo-chromene nucleus. To further exemplify the invention, this ring is depicted below along with its numbering system:

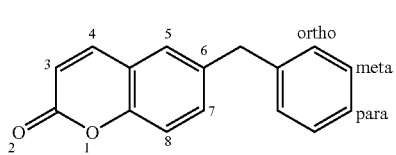

Ib

Position 1 of the chromene nucleus contains an oxygen atom. Position 6 of the chromene ring will always be substituted with a benzyl moiety as depicted in FIG. Ib. Any of Positions 3, 5, 7, or 8 of the chromene nucleus may optionally be substituted with a substituent from the list described for $R^2$. Up to two of these positions may be substituted. Position 4 of the chromene nucleus may optionally be substituted with one of the halogenated lower alkyl or alkoxy moieties described for $R^1$ above. Typically, Position 4 will be substituted with a trifluoromethyl function.

The benzyl moiety adjacent to position 6 will be further substituted with a will be further substituted with a sulfonamide moiety (—$SO_2$—NAB). The sulfonamide moiety may be attached to the ortho, meta, or para position of the benzyl ring (typically para).

More specific embodiments of the invention are directed to compounds of Formula I in which:

a) M is represented by N, in which Z is hydrogen, $R^1$ is represented trifluoromethyl, the sulfonamide function is located at the para-position of the benzyl ring, A is $C_1$–$C_6$alkyl$R^6$, and B is hydrogen or $C_1$–$C_6$alkyl.

b) M is represented by N, in which Z is hydrogen, $R^1$ is represented trifluoromethyl, the sulfonamide function is located at the para-position of the benzyl ring, A is hydrogen or $C_1$–$C_6$alkyl$R^6$, and B is optionally substituted cycloalkyl, optionally substituted cycloalkenyl, optionally substituted phenyl, optionally substituted cycloalkylphenyl, optionally substituted heteroaryl or optionally substituted heterocycle.

c) M is represented by N, in which Z is hydrogen, $R^1$ is represented trifluoromethyl, the sulfonamide function is located at the para-position of the benzyl ring, A is hydrogen or $C_1$–$C_6$alkyl, and B is phenyl, which may be optionally substituted.

d) M is represented by N, in which Z is hydrogen, $R^1$ is represented trifluoromethyl, the sulfonamide function is located at the para-position of the benzyl ring, A is optionally substituted phenyl, and B is hydrogen e) M is represented by O, $R^1$ is represented trifluoromethyl, the sulfonamide function is located at the para-position of the benzyl ring, A is $C_1$–$C_6$alkyl$R^6$, and B is hydrogen or $C_1$–$C_6$alkyl.

f) M is represented by O, $R^1$ is represented trifluoromethyl, the sulfonamide function is located at the para-position of the benzyl ring, A is hydrogen or $C_1$–$C_6$alkyl$R^6$, and B is optionally substituted cycloalkyl, optionally substituted phenyl, optionally substituted cycloalkylphenyl, optionally substituted heteroaryl or optionally substituted heterocycle.

g) M is represented by O, $R^1$ is represented trifluoromethyl, the sulfonamide function is located at the para-position of the benzyl ring, A is hydrogen or $C_1$–$C_6$alkyl, and B is phenyl, which may be optionally substituted.

B) Synthesis

The compounds of formula can be prepared using methods analogous to those known in the art. Reaction Scheme I describe one method for the synthesis of these compounds:

Reaction Scheme I

A) Step A

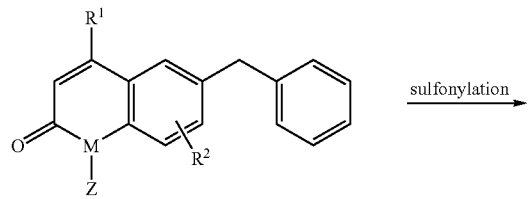

B) Step B

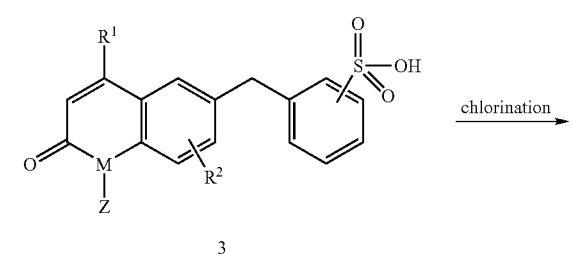

C) Step C

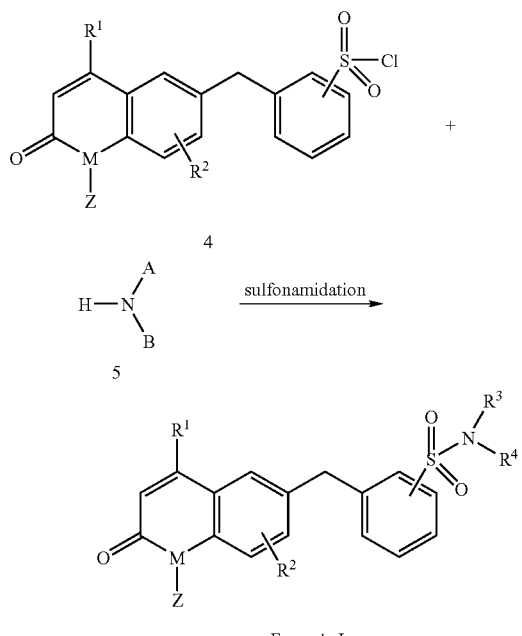

The starting material, as described by structure 2, is an appropriately substituted 6-benzyl-quinolin-2-one or 6-benzyl-chromen-2-one (i.e. M, $R^1$ and $R^2$ should be represented by the substituents desired in the final product). Such compounds are known in the art. The reader's attention is directed to Kondedesh-mukah et al, Indian J. Chemistry, Sect. B 1993, 32, 1150–1161, for a discussion of their preparation. The working examples, appearing later in the specification, describe the synthesis of 4-trifluoromethyl-6-benzyl-quinolin-2-one and 4-trifluromethyl-6-benzyl-chromen-2-one.

The initial step in the synthesis is the incorporation of a sulfonic acid function at the relevant position of the benzyl moiety as depicted above (i.e $SO_3H$). This sulfonylation may be accomplished by a number of methods. One suitable method is to contact the quinoline or chromene derivative with sulfuric acid. Typically, the compound of structure 2 is stirred with concentrated sulfuric acid at temperatures ranging from 0° C. to about 90° C. The reaction is allowed to proceed to completion, which may be accomplished in a period of time ranging from about 15 minutes to about 1 hour, or longer. The product of the sulfonylation reaction may be isolated and purified by techniques known in art, or the crude isolate may be used directly in the next step of synthesis. Readers can find more information on sulfonylation techniques in J. March, Advanced Organic Chemistry, 3$^{rd}$ edition, pages 473–475, John Wiley & Sons (1985).

The second step of the synthesis is to transform the sulfonic acid of structure 3 into a sulfonyl chloride as depicted by structure 4. This may be accomplished, as is known in the art, by contacting the sulfonic acid derivative of structure 3 with a halogenating agent. Typically, the sulfonic acid derivative of structure 3 is contacted with a solution of oxalyl chloride in a chlorinated solvent such as methylene chloride, and in the presence of a catalyst, such as N,N-dimethylformamide. The reaction is carried out at room temperature and is allowed to proceed to completion, which is generally accomplished in about 30 minutes. The product of the chlorination reaction may be isolated and purified by techniques known in art, or the crude isolate may be used directly in the next step of synthesis. Readers can find more information on the preparation of sulfonyl chlorides in J. March, Advanced Organic Chemistry, 3$^{rd}$ edition, page 445, John Wiley & Sons (1985).

The final step in the synthesis results in the preparation of the sulfonamide derivative of Formula I. This may be accomplished by reacting the sulfonyl chloride of structure 4 with a nitrogen nucleophile as described by structure 5 in the presence of a non-nucleophilic base, such as pyridine or diisopropylethylamine, at about room temperature in an aprotic solvent, such as, N,N'-dimethylformamide. The reaction is allowed to proceed to completion, which is typically accomplished in about 2 to 24 hours. If desired, the compounds can be isolated and purified using techniques known in the art such as extraction and flash chromatography. The reader's attention is also directed to J. March, Advanced Organic Chemistry, 3$^{rd}$ edition, page 445, John Wiley & Sons (1985) for an overview regarding the preparation of sulfonamides The nitrogen nucleophile, as described by structure 5, provides the appropriately substituted amine (i.e. —NAB), which is incorporated into all of the compounds of Formula I. In this amine, A and B should be represented by the substituents that are desired in final product. These amines can typically be purchased from Aldrich, which has an office located in St. Louis, Mo. USA. Further information may be obtained from Aldrich at, www.sigmaaldrich.com Medical and Cosmetic Uses The compounds of Formula I are androgen receptor antagonists. They can be used to alleviate any condition associated with inappropriate activation of the androgen receptor. Examples of such conditions include prostate carcinomas, benign hyperplasia of the prostate, acne, hirsutism, seborrhoea, alopecia, premenstrual syndrome, lung cancer, and precocious puberty.

In order to exhibit the therapeutic properties described above, the compounds need to be administered in a quantity sufficient to inhibit activation of the androgen receptor. This antagonistic amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally), rectally, or topically.

In a typical embodiment, the compounds are administered topically. Topical administration is especially appropriate for hirsutism, alopecia, acne and hyperseborhhea. The dose will vary, but as a general guideline, the compound will be present in a dermatologically acceptable carrier in an amount of from 0.1 to 10 w/w % and the dermatological preparation will be applied to the affected area from 1 to 4 times daily. "Dermatologically acceptable" refers to a carrier which may be applied to the skin or hair, and which will allow the drug to diffuse to the site of action. More specifically, it refers to the site where inhibition of activation of an androgen receptor is desired. In a further embodiment, the compounds are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. Men castrated before puberty fail to grow beards and do not go bald. If subsequently treated with testosterone about one third of male castrates will show balding. Androgeneic alopecia is also common in women where it usually present as a diffuse hair loss rather than showing the patterning seen in men.

As used in this application "alopecia" refers to partial or complete hair loss on the scalp. The compounds will typically be used to alleviate androgenic alopecia. This condition afflicts both men and women. In males, the hair loss begins in the lateral frontal areas or over the vertex. For females, it is typically associated with thinning of the hair in the frontal and parietal regions. Complete hair loss in females is rare.

While the compounds will most typically be used to alleviate androgenic alopecia, the invention is not limited to this specific condition. The compounds may be used to alleviate any type of alopecia. Examples of non-androgenic alopecia include alopecia areata, alopecia due to radiotherapy or chemotherapy, scarring alopecia, stress related alopecia, etc.

Thus, the compounds can be applied topically to the scalp and hair to prevent, or alleviate balding. Further, the compound can be applied topically in order to induce or promote the growth of hair on the scalp.

In a further embodiment of the invention, a compound of Formula I is applied topically in order to prevent the growth of hair in areas where such hair growth is not desired. One such use will be to alleviate hirsutism. Hirsutism is excessive hair growth in areas that typically do not have hair (i.e. a female face). Such inappropriate hair growth occurs most commonly in women and is frequently seen at menopause. The topical administration of the compounds will alleviate this condition leading to a reduction, or elimination of this inappropriate, or undesired, hair growth.

The compounds may also be used topically to decrease seborrhea production and more specifically to alleviate hyperseborrhoea (oily skin). Likewise the compounds can be used topically alleviate acne.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair.

Pharmaceutical and cosmetic compositions can be manufactured utilizing techniques known in the art. Typically an antagonistic amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin or hair. The topical composition according to the present invention can be in the form of solutions, lotions, salves, creams, ointments, liposomes, sprays, gels, roller sticks, or any other method using micelles and pharmaceutically acceptable penetration enhancers Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily.

The compositions according to the invention can also consist of solid preparations constituting cleansing soaps or bars. These compositions are prepared according to the usual methods.

The compounds can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition (in particular an oxidation dye composition) optionally in the form of coloring shampoos, restructuring lotions for the hair, a permanent-waving composition (in particular a composition for the first stage of a permanent-waving operation), a lotion or gel for preventing hair loss, etc. The amounts of the various constituents in the dermatological compositions according to the invention are those conventionally used in the fields considered.

The medicinals and cosmetics containing the compounds of the invention will typically be packaged for retail distribution (i.e. an article of manufacture). Such articles will be labeled and packaged in a manner to instruct the patient how to use the product. Such instructions will include the condition, which may be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data is being presented in order to further illustrate the invention. This disclosure should not be construed as limiting the invention in any manner.

EXAMPLES

Materials & Methods

Column chromatography was carried out on $SiO_2$ (40–63 mesh). LCMS data were obtained using a Phenomenex Mercury Luna 3μ $C^{18}$ column (2×10 mm, flow rate=1.5 mL min−1) eluting with a 5% MeCN in $H_2O$—MeCN solution (4:1 to 1:4) containing 0.1% $HCO_2H$ over 2.55 min & diode array detection. The mass spectra were obtained employing an electrospray ionization source in the positive (ES+) & negative (ES−) ion modes. Preparative mass-directed liquid chromatographic purification was carried out utilizing a Waters Xterra 5μ $C^{18}$ column (19×50 mm, flow rate=20 mL min−1) eluting with a 5% MeCN in $H_2O$—MeCN solution (4:1 to 1:4) containing 0.1% $HCO_2H$ over 7 min & diode array detection. $^1H$ NMR spectra were recorded at 400 MHz on a Varian Mercury spectrometer at 27° C. The deuterated solvent was used as the lock, while the residual solvent peak was employed as internal reference. Acronyms: DMAP=4-dimethylaminopyridine; HATU=O-(7-azabenzotriazol-1-yl)-N,N,N',N'-tetramethyluronium hexafluorophosphate; NMP=1-methyl-2-pyrrolidinone; PE=petroleum ether (B.p.=60–80° C.); RT=retention time Preparation #1

4-(2-Oxo-4-trifluoromethyl-1,2-dihydroquinolin-6-ylmethyl)-benzenesulfonyl chloride

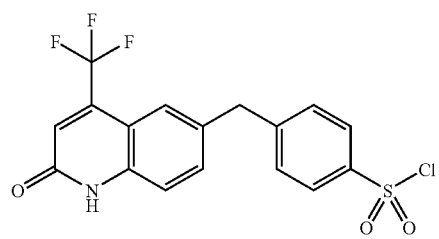

A stirred solution of 4-benzylaniline (4.03 g, 22.0 mmol) in PhMe (100 mL) was treated with a PhMe (20 mL) solution of $CF_3COCH_2CO_2Et$ (4.15 g, 22.5 mmol). The reaction mixture was heated under reflux for 30 min, then more $CF_3COCH_2CO_2Et$ (1.25 g, 6.8 mmol) was added. The solution was heated under reflux for a further 2 h & the solvent removed under reduced pressure. The residual brown oil was dissolved in cold $H_2SO_4$ (30 mL), then the mixture was heated at 90° C. for 1 h. On cooling, the reaction mixture was poured onto crushed ice (100 g). The solid produced was collected & dried to give 4-(2-oxo-4-trifluoromethyl-1,2-dihydroquinolin-6-ylmethyl)-benzenesulfonic acid (4.70 g, 56%): $\delta_H$ $((CD_3)_2SO)$=6.95 (s, 1H), 7.20 (d, 2 H), 7.40 (d, 1H), 7.45–7.60 (m, 4H). A vigourously stirred solution of this compound (1.92 g, 5.0 mmol) in anhydrous $CH_2Cl_2$—DMF (2:1, 60 mL) was treated dropwise with a solution of $(COCl)_2$ (3.17 g, 25.0 mmol) in anhydrous $CH_2Cl_2$ (47 mL). When LCMS indicated the reaction was complete, the solution was concentrated & the residue dissolved in $Et_2O$ (250 mL). The $Et_2O$ solution was washed with $H_2O$ (80 mL), back-extracting with more $Et_2O$ (80 mL). The combined organic extracts were dried ($MgSO_4$), filtered, & concentrated. The residue was treated with PE & the title compound (1.41 g, 70%) collected: m/z $(ES^+)$=402.1 $[M+H]^+$.

Preparation #2

4-(2-Oxo-4-trifluoromethyl-2H-chromen-6-ylmethyl)benzene-sulfonyl chloride

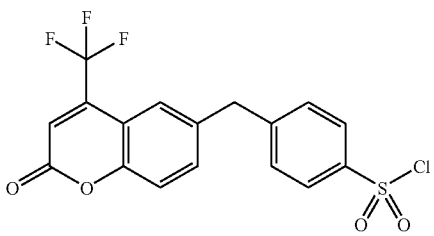

A stirred suspension of 4-benzylphenol (4.67 g, 25.4 mmol), $CF_3COCH_2CO_2Et$ (7.00 g, 38.0 mmol), & $MeSO_3H$ (8.5 mL, 130.9 mmol) was heated at 65° C. for 9 h. On cooling, the mixture was partitioned between $Et_2O$ (200 mL) & $H_2O$ (50 mL), then the aqueous phase was basicified with 2 M NaOH. The organic layer was separated & washed with $H_2O$ & brine, before being dried (MgSO4). Filtration, solvent evaporation, & column chromatography (4:1 PE-$Et_2O$) furnished 6-benzyl4-trifluoromethylchromen-2-one (3.42 g, 44%): $\delta_H$ ($CDCl_3$)=4.10 (s, 2H), 6.85 (s, 1H), 7.20–7.40 (m, 5H), 7.45 (dd, 1H), 7.60 (d, 1H). This compound (2.00 g, 6.6 mmol) was dissolved in $H_2SO_4$ (20 mL), then the whole was stirred for 15 min. The mixture was carefully treated with crushed ice (80 g), then the resulting white precipitate was collected by filtration. The precipitate was air-dried, before being treated with hot THF (100 mL). After filtration, the filtrate was concentrated to yield 4-(2-oxo-4-trifluoromethyl-2H-chromen-6-ylmethyl)benzenesulfonic acid (2.20 g, 87%): $\delta_H$ $((CD_3)_2SO)$=4.05 (s, 2H), 7.00 (s, 1H), 7.20 (d, 2H), 7.45 (d, 1H), 7.50–7.60 (m, 4H). This compound was reacted with $(COCl)_2$, as described above in Preparation 1, to give a solid which was dissolved in EtOAc, before being filtered & concentrated to produce the title compound (2.30 g, 87%): $R_f$ (2:1 PE-EtOAc)=0.60.

Example 1

N-Isopropyl-4-(2-oxo4-trifluoromethyl-1,2-dihydroquinolin-6-ylmethyl)benzenesulfonamide

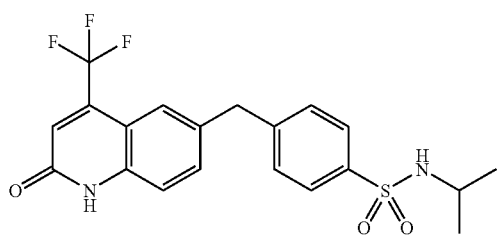

A stirred solution of 4-(2-oxo4-trifluoromethyl-1,2-dihydroquinolin-6-ylmethyl)-benzenesulfonyl chloride (Preparation 1, 17 mg, 42 µmol) in anhydrous $CH_2Cl_2$ (0.5 mL) was treated dropwise with an excess of i-$PrNH_2$ (145 µL, 1680 µmol). After stirring at 20° C. for 10 min, the reaction mixture was submitted to column chromatography (EtOAc) to furnish the title compound (8 mg, 45%): $\delta_H$ ($CD_3OD$) =1.00 (d, 6H), 3.35 (sept, 1H), 4.20 (s, 2H), 7.00 (s, 1H), 7.15–7.20 (m, 3H), 7.50 (dd, 1H), 7.60 (d, 1H), 7.80 (d, 2H); m/z $(ES^+)$=466.1 $[M+H+MeCN]^+$.

Example 2

N-Butyl-4-(2-oxo-4-trifluoromethyl-1,2-dihydroquinolin-6-ylmethyl)benzenesulfonamide

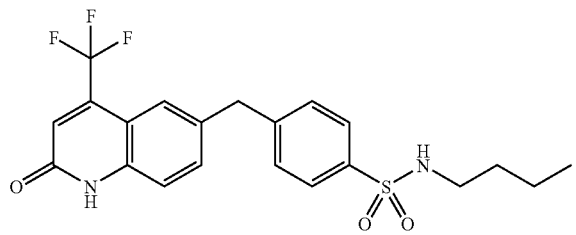

4-(2-oxo-4-trifluoromethyl-1,2-dihydroquinolin-6-ylmethyl)benzenesulfonyl chloride (Preparation 1, 26 mg, 65 µmol) was reacted with an excess of n-$BuNH_2$ (190 mg, 2600 µmol) by the same procedure used for Example 1. After reaction, the solvents were evaporated off under reduced pressure & the residue partitioned between EtOAc (10 mL) & 2 M HCl (3 mL). The organic phase was washed with $H_2O$ (2 mL), 1 M NaOH (3 mL), & brine (2 mL), before being dried ($MgSO_4$). Filtration & solvent evaporation furnished the title compound (26 mg, 84%): $\delta_H$ $((CD_3)_2SO)$ =0.75 (t, 3H), 1.20–1.35 (m, 4H), 2.65 (m, 2H), 4.15 (s, 2H), 6.95 (s, 1H), 7.35–7.55 (m, 5H), 7.70 (d, 2H); m/z (ES⁺) =480.2 [M+H+MeCN]⁺.

Example 3

N-Benzyl-4-(2-oxo-4-trifluoromethyl-1,2-dihydro-quinolin-6-ylmethyl)benzenesulfonamide

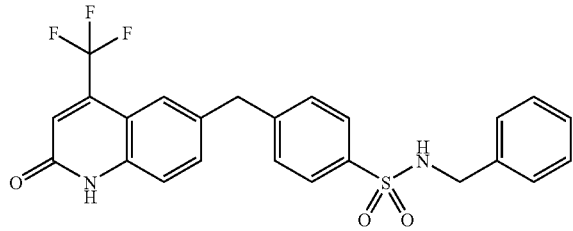

Reaction of 4-(2-oxo-4-trifluoromethyl-1,2-dihydro-quinolin-6-ylmethyl)benzene-sulfonyl chloride (Preparation 1, 26 mg, 65 μmol) with an excess of BnNH₂ (280 mg, 2600 μmol), by the method described for Example 1, generated the title compound (19 mg, 61%): δ$_H$ ((CD₃)₂SO)=3.95 (d, 2H), 4.15 (s, 2H), 7.00 (s, 1H), 7.15–7.25 (m, 5H), 7.35–7.45 (m, 3H), 7.50 (d, 1H), 7.55 (s, 1H), 7.70 (d, 2H), 8.05 (t, 1H); m/z (ES⁺)=514.2 [M+H +MeCN]⁺.

Examples 4–209

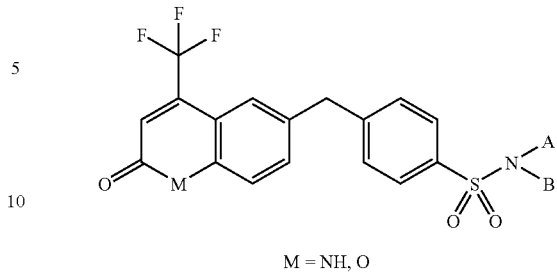

M = NH, O

These compounds were prepared by solution phase parallel synthesis. The appropriate amine as described by structure 5 above (30 μL of a 0.33 M solution NMP, 9.9 μmol), i-Pr₂NEt (20 μL of a 0.50 M solution in NMP, 10.0 μmol), & the sulfonyl chloride as described by structure 4 above (50 μL of a 0.20 M solution in NMP, 10.0 μmol) were mixed together in 1 well of a 96-well plate using an automated liquid handler. After agitating for 66 h, the solvents were evaporated off under reduced pressure & DMF (50 μL) was added. To ensure 15 dissolution, the mixture was shaken, before being treated with EtOAc (450 μL). Using automated liquid-liquid extraction equipment, the solution was washed with H₂O (150 μL) & 1% aqueous NaHCO₃ (150 μL). The organic layer was concentrated to furnish the compounds displayed in Table 1 immediately below.

| Example | CHEMISTRY | Name | RT | Base Peak |
|---|---|---|---|---|
| 4 | | N-Cyclohexyl-N-(2-hydroxyethyl)-4-(2-oxo-4-trifluoromethyl-1,2-dihydroquinolin-6-ylmethyl)benzenesulfonamide | 1.82 | 509.2 [M + H]$^+$ |
| 5 | | N-Ethyl-4-(2-oxo-4-trifluoro methyl-1,2-dihydroquinolin-6-ylmethyl)-N-pyridin-4-ylmethylbenzenesulfonamide | 1.43 | 500.2 [M − H]$^-$ |
| 7 | | N-Isopropyl-N-methyl-4-(2-oxo-4-trifluoromethyl-1,2-dihydroquinolin-6-ylmethyl)benzenesulfonamide | 1.89 | 437.2 [M − H]$^-$ |

| Example | CHEMISTRY | Name | RT | Base Peak |
|---|---|---|---|---|
| 8 | 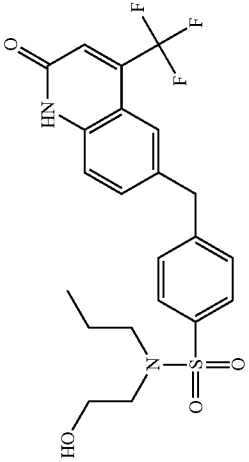 | N-(2-Hydroxyethyl)-4-(2-oxo-4-trifluoromethyl-1,2-dihydroquinolin-6-ylmethyl)-N-propylbenzenesulfonamide | 1.70 | 469.2 [M + H]$^+$ |
| 9 | 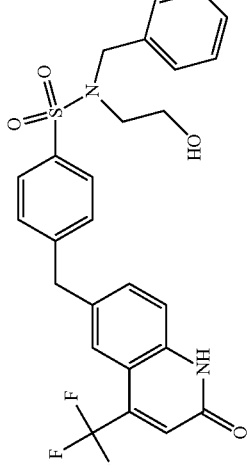 | N-Benzyl-N-(2-hydroxyethyl)-4-(2-oxo-4-trifluoromethyl-1,2-dihydroquinolin-6-ylmethyl)benzenesulfonamide | 1.81 | 517.2 [M + H]$^+$ |
| 9A | 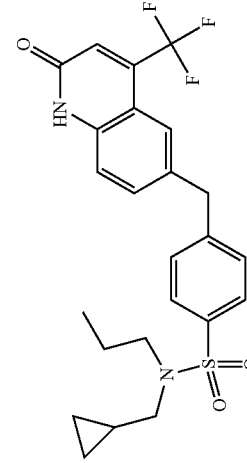 | N-Cyclopropylmethyl-4-(2-oxo-4-trifluoromethyl-1,2-dihydroquinolin-6-ylmethyl)-N-propylbenzenesulfonamide | 2.04 | 479.2 [M + H]$^+$ |
| 9B | 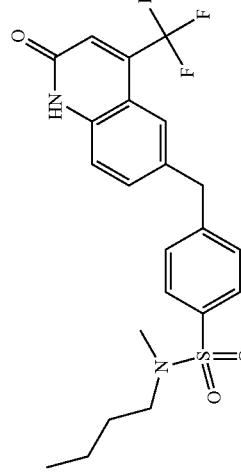 | N-Butyl-N-methyl-4-(2-oxo-4-trifluoromethyl-1,2-dihydroquinolin-6-ylmethyl)benzenesulfonamide | 1.96 | 453.2 [M + H]$^+$ |

-continued

| Example | CHEMISTRY | Name | RT | Base Peak |
|---|---|---|---|---|
| 10 | | N-(2-Cyanoethyl)-N-methyl-4-(2-oxo-4-trifluoromethyl-1,2-dihydroquinolin-6-ylmethyl)benzenesulfonamide | 1.71 | 491.2 [M + H + MeCN]$^+$ |
| 11 | | N,N-Dibenzyl-4-(2-oxo-4-trifluoromethyl-1,2-dihydroquinolin-6-ylmethyl)benzenesulfonamide | 2.16 | 563.2 [M + H]$^+$ |
| 12 | | N,N-Bis(2-methoxyethyl)-4-(2-oxo-4-trifluoromethyl-1,2-dihydroquinolin-6-ylmethyl)benzenesulfonamide | 1.72 | 499.2 [M + H]$^+$ |

-continued

| Example | CHEMISTRY | Name | RT | Base Peak |
|---|---|---|---|---|
| 13 | 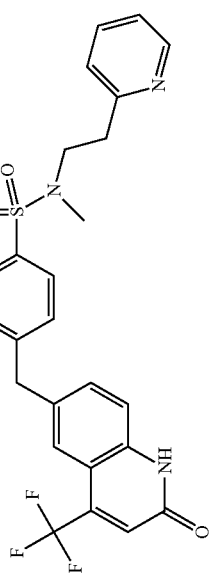 | N-Methyl-4-(2-oxo-4-trifluoromethyl-1,2-dihydroquinolin-6-ylmethyl)-N-(2-pyridin-2-ylethyl)benzenesulfonamide | 1.40 | 502.2 [M + H]+ |
| 14 | 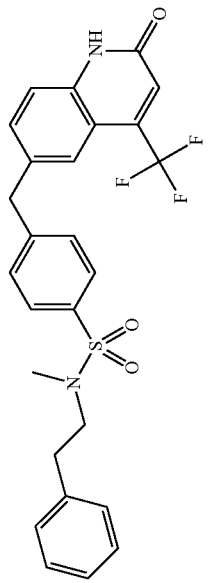 | N-Methyl-4-(2-oxo-4-trifluoromethyl-1,2-dihydroquinolin-6-ylmethyl)-N-phenethylbenzenesulfonamide | 2.00 | 501.2 [M + H]+ |
| 15 | 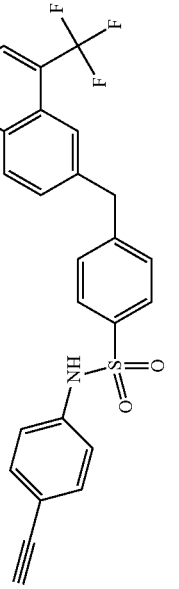 | N-(4-Ethynylphenyl)-4-(2-oxo-4-trifluoromethyl-1,2-dihydroquinolin-6-ylmethyl)benzenesulfonamide | 1.88 | 481.1 [M − H]− |
| 16 | 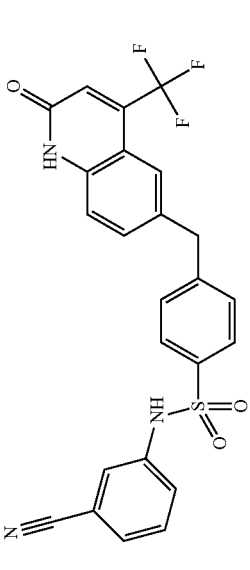 | N-(3-Cyanophenyl)-4-(2-oxo-4-trifluoromethyl-1,2-dihydroquinolin-6-ylmethyl)benzenesulfonamide | 1.78 | 482.2 [M − H]− |

-continued

| Example | CHEMISTRY | Name | RT | Base Peak |
|---|---|---|---|---|
| 17 | | N-(3-Ethylphenyl)-4-(2-oxo-4-trifluoromethyl-1,2-dihydroquinolin-6-ylmethyl)benzenesulfonamide | 1.94 | 485.2 [M − H]− |
| 18 | | N-(2-Chlorophenyl)-4-(2-oxo-4-trifluoromethyl-1,2-dihydroquinolin-6-ylmethyl)-benzenesulfonamide | 1.88 | 491.1 [M − H]− |
| 19 | | 4-(2-Oxo-4-trifluoromethyl-1,2-dihydroquinolin-6-ylmethyl)-N-quinolin-6-ylbenzenesulfonamide | 1.48 | 510.2 [M + H]+ |
| 20 | | N-Indan-5-yl-4-(2-oxo-4-trifluoromethyl-1,2-dihydroquinolin-6-ylmethyl)-benzenesulfonamide | 1.94 | 497.2 [M − H]− |

| Example | CHEMISTRY | Name | RT | Base Peak |
|---|---|---|---|---|
| 21 | | N-(3-Acetylphenyl)-4-(2-oxo-4-trifluoromethyl-1,2-dihydroquinolin-6-ylmethyl)benzenesulfonamide | 1.74 | 499.2 [M − H]⁻ |
| 22 | | N-(4-Methylbiphenyl-3-yl)-4-(2-oxo-4-trifluoromethyl-1,2-dihydroquinolin-6-ylmethyl)-benzenesulfonamide | 2.02 | 547.2 [M − H]⁻ |
| 23 | | N-[3-(1-Hydroxyethyl)phenyl]-4-(2-oxo-4-trifluoromethyl-1,2-dihydroquinolin-6-ylmethyl)-benzenesulfonamide | 1.69 | 501.2 [M − H]⁻ |

-continued

| Example | CHEMISTRY | Name | RT | Base Peak |
|---|---|---|---|---|
| 24 | | N-(3-Methylsulfanylphenyl)-4-(2-oxo-4-trifluoromethyl-1,2-dihydroquinolin-6-ylmethyl)-benzenesulfonamide | 1.88 | 503.1 [M − H]$^-$ |
| 26 | | N-(4-Chlorophenyl)-4-(2-oxo-4-trifluoromethyl-1,2-dihydroquinolin-6-ylmethyl)-benzenesulfonamide | 1.92 | 491.1 [M − H]$^-$ |
| 27 | | N-Isoquinolin-3-yl-4-(2-oxo-4-trifluoromethyl-1,2-dihydroquinolin-6-ylmethyl)-benzenesulfonamide | 1.79 | 510.2 [M + H]$^+$ |
| 28 | | 4-(2-Oxo-4-trifluoromethyl-1,2-dihydroquinolin-6-ylmethyl)-N-quinolin-3-ylbenzenesulfonamide | 1.75 | 510.2 [M + H]$^+$ |

-continued

| Example | CHEMISTRY | Name | RT | Base Peak |
|---|---|---|---|---|
| 29 | | 4-(2-Oxo-4-trifluoromethyl-1,2-dihydroquinolin-6-ylmethyl)-N-quinolin-5-ylbenzenesulfonamide | 1.53 | 510.2 [M + H]+ |
| 30 | | 4-(2-Oxo-4-trifluoromethyl-1,2-dihydroquinolin-6-ylmethyl)-N-quinolin-8-ylbenzenesulfonamide | 1.91 | 510.2 [M + H]+ |
| 31 | | N-Isoquinolin-5-yl-4-(2-oxo-4-trifluoromethyl-1,2-dihydroquinolin-6-ylmethyl)-benzenesulfonamide | 1.50 | 5.10 [M + H]+ |

| Example | CHEMISTRY | Name | RT | Base Peak |
|---|---|---|---|---|
| 32 | 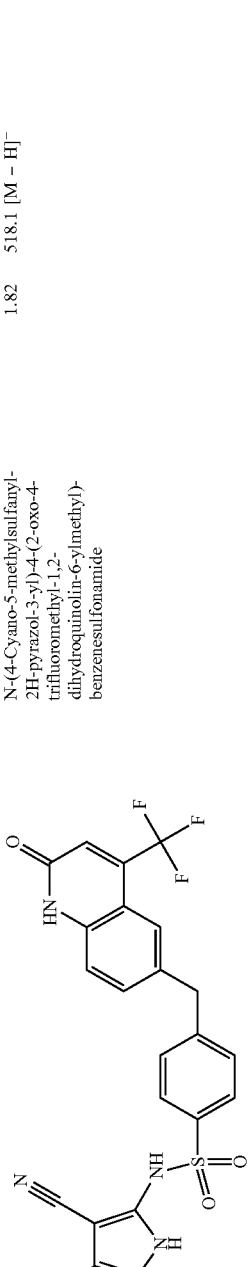 | N-(4-Cyano-5-methylsulfanyl-2H-pyrazol-3-yl)-4-(2-oxo-4-trifluoromethyl-1,2-dihydroquinolin-6-ylmethyl)-benzenesulfonamide | 1.82 | 518.1 [M − H]− |
| 33 | 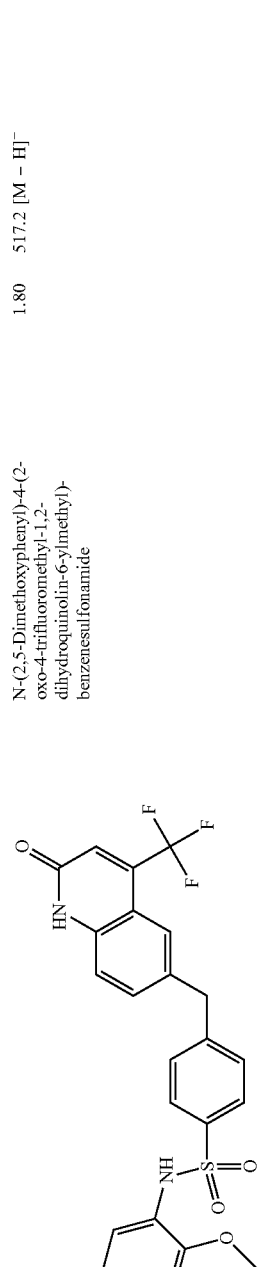 | N-(2,5-Dimethoxyphenyl)-4-(2-oxo-4-trifluoromethyl-1,2-dihydroquinolin-6-ylmethyl)-benzenesulfonamide | 1.80 | 517.2 [M − H]− |
| 34 | 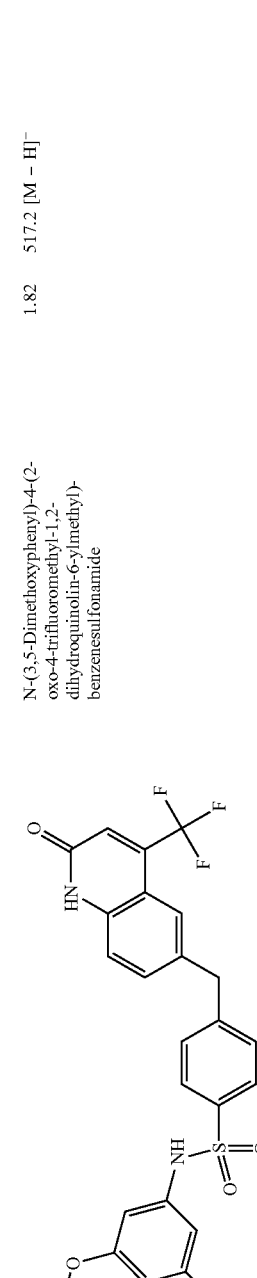 | N-(3,5-Dimethoxyphenyl)-4-(2-oxo-4-trifluoromethyl-1,2-dihydroquinolin-6-ylmethyl)-benzenesulfonamide | 1.82 | 517.2 [M − H]− |
| 35 | 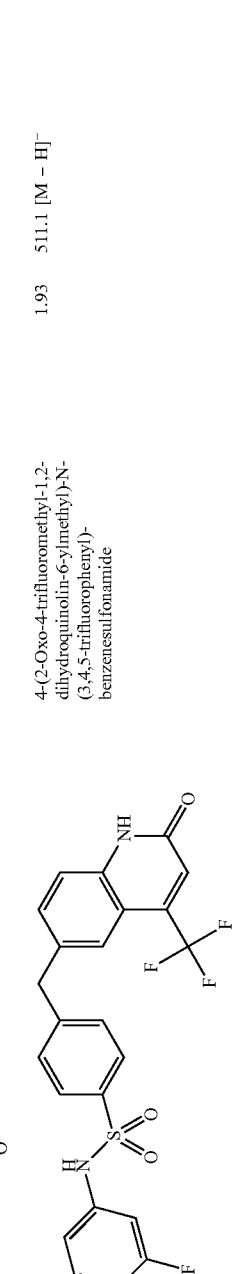 | 4-(2-Oxo-4-trifluoromethyl-1,2-dihydroquinolin-6-ylmethyl)-N-(3,4,5-trifluorophenyl)-benzenesulfonamide | 1.93 | 511.1 [M − H]− |

-continued

| Example | CHEMISTRY | Name | RT | Base Peak |
|---|---|---|---|---|
| 36 | | N-(3-Difluoromethoxyphenyl)-4-(2-oxo-4-trifluoromethyl-1,2-dihydroquinolin-6-ylmethyl)-benzenesulfonamide | 1.89 | 525.1 [M + H]$^+$ |
| 37 | | 4-(2-Oxo-4-trifluoromethyl-1,2-dihydroquinolin-6-ylmethyl)-N-(5-phenyl-2H-pyrazol-3-yl)-benzenesulfonamide | 1.75 | 525.2 [M + H]$^+$ |
| 38 | | N-(3-Oxazol-5-ylphenyl)-4-(2-oxo-4-trifluoromethyl-1,2-dihydroquinolin-6-ylmethyl)benzenesulfonamide | 1.72 | 524.2 [M − H]$^-$ |

-continued

| Example | CHEMISTRY | Name | RT | Base Peak |
|---|---|---|---|---|
| 39 | | 4-(2-Oxo-4-trifluoromethyl-1,2-dihydroquinolin-6-ylmethyl)-N-(3-trifluoromethylphenyl)-benzenesulfonamide | 1.95 | 525.1 [M − H]− |
| 40 | | N-(2-Bromophenyl)-4-(2-oxo-4-trifluoromethyl-1,2-dihydroquinolin-6-ylmethyl)-benzenesulfonamide | 1.91 | 539.0 [M + H]+ |
| 41 | | 4-(2-Oxo-4-trifluoromethyl-1,2-dihydroquinolin-6-ylmethyl)-N-(2-piperidin-1-ylphenyl)-benzenesulfonamide | 2.04 | 542.2 [M + H]+ |
| 42 | | 4-(2-Oxo-4-trifluoromethyl-1,2-dihydroquinolin-6-ylmethyl)-N-(3-trifluoromethoxyphenyl)-benzenesulfonamide | 1.98 | 541.1 [M − H]− |

| Example | CHEMISTRY | Name | RT | Base Peak |
|---|---|---|---|---|
| 43 | | N-(3-Benzylphenyl)-4-(2-oxo-4-trifluoromethyl-1,2-dihydroquinolin-6-ylmethyl)-benzenesulfonamide | 1.99 | 547.2 [M − H]⁻ |
| 44 | | N-(3-Benzyloxyphenyl)-4-(2-oxo-4-trifluoromethyl-1,2-dihydroquinolin-6-ylmethyl)-benzenesulfonamide | 2.02 | 563.2 [M − H]⁻ |
| 45 | | N-Benzyl-N-(4-methoxyphenyl)-4-(2-oxo-4-trifluoromethyl-1,2-dihydroquinolin-6-ylmethyl)-benzenesulfonamide | 2.07 | 577.2 [M − H]⁻ |

| Example | CHEMISTRY | Name | RT | Base Peak |
|---|---|---|---|---|
| 46 |  | N-{2-[(Cyclohexylmethyl-amino)methyl]phenyl}-4-(2-oxo-4-trifluoromethyl-1,2-dihydroquinolin-6-ylmethyl)-benzenesulfonamide | 1.49 | 584.3 [M + H]$^+$ |
| 47 | 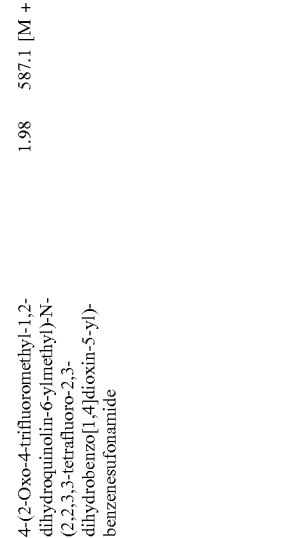 | 4-(2-Oxo-4-trifluoromethyl-1,2-dihydroquinolin-6-ylmethyl)-N-(2,2,3,3-tetrafluoro-2,3-dihydrobenzo[1,4]dioxin-5-yl)-benzenesulfonamide | 1.98 | 587.1 [M + H]$^-$ |
| 48 | 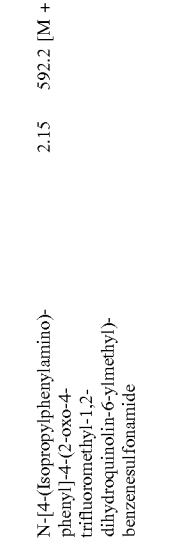 | N-[4-(Isopropylphenylamino)-phenyl]-4-(2-oxo-4-trifluoromethyl-1,2-dihydroquinolin-6-ylmethyl)-benzenesulfonamide | 2.15 | 592.2 [M + H]$^+$ |

-continued

| Example | CHEMISTRY | Name | RT | Base Peak |
|---|---|---|---|---|
| 49 | | 4-(2-Oxo-4-trifluoromethyl-1,2-dihydroquinolin-6-ylmethyl)-N-[4-(3-trifluoromethylpyrazol-1-yl)phenyl]-benzenesulfonamide | 1.94 | 591.1 [M − H]⁻ |
| 50 | | N-(3-Methoxyphenyl)-4-(2-oxo-4-trifluoromethyl-1,2-dihydroquinolin-6-ylmethyl)-benzenesulfonamide | 1.83 | 487.1 [M − H]⁻ |
| 51 | | N-(2-Hydroxyethyl)-4-(2-oxo-4-trifluoromethyl-1,2-dihydroquinolin-6-ylmethyl)-benzenesulfonamide | 1.50 | 425.2 [M − H]⁻ |
| 52 | | N-(1-Benzylpipeidin-4-yl)-4-(2-oxo-4-trifluoromethyl-1,2-dihydroquinolin-6-ylmethyl)-benzenesulfonamide | 1.35 | 556.2 [M + H]⁺ |

| Example | CHEMISTRY | Name | RT | Base Peak |
|---|---|---|---|---|
| 53 | | N-(2-Methoxyethyl)-4-(2-oxo-4-trifluoromethyl-1,2-dihydroquinolin-6-ylmethyl)-benzenesulfonamide | 1.63 | 439.2 [M − H]⁻ |
| 54 | | N-(3,3-Dimethylbutyl)-4-(2-oxo-4-trifluoromethyl-1,2-dihydroquinolin-6-ylmethyl)-benzenesulfonamide | 1.92 | 465.2 [M − H]⁻ |
| 55 | | N-(5-Methylfuran-2-ylmethyl)-4-(2-oxo-4-trifluoromethyl-1,2-dihydroquinolin-6-ylmethyl)-benzenesulfonamide | 1.81 | 475.2 [M − H]⁻ |
| 56 | | 4-(2-Oxo-4-trifluoromethyl-1,2-dihydroquinolin-6-ylmethyl)-N-(2-pyrrolidin-1-yl-ethyl)-benzenesulfonamide | 1.31 | 480.2 [M + H]⁺ |

-continued

| Example | CHEMISTRY | Name | RT | Base Peak |
|---|---|---|---|---|
| 57 | | 4-(2-Oxo-4-trifluoromethyl-1,2-dihydroquinolin-6-ylmethyl)-N-phenethylbenzenesulfonamide | 1.87 | 485.2 [M − H]⁻ |
| 58 | | N-(3-Methylbenzyl)-4-(2-oxo-4-trifluoromethyl-1,2-dihydroquinolin-6-ylmethyl)-benzenesulfonamide | 1.92 | 485.2 [M − H]⁻ |
| 59 | | 4-(2-Oxo-4-trifluoromethyl-1,2-dihydroquinolin-6-ylmethyl)-N-(2-pyridin-2-ylethyl)-benzenesulfonamide | 1.35 | 488.2 [M + H]⁺ |

| Example | CHEMISTRY | Name | RT | Base Peak |
|---|---|---|---|---|
| 60 | | N-(3-Imidazol-1-ylpropyl)-4-(2-oxo-4-trifluoromethyl-1,2-dihydroquinolin-6-ylmethyl)-benzenesulfonamide | 1.33 | 491.2 [M + H]$^+$ |
| 61 | | N-(2-Cyclohex-1-enylethyl)-4-(2-oxo-4-trifluoromethyl-1,2-dihydroquinolin-6-ylmethyl)-benzenesulfonamide | 2.00 | 489.2 [M − H]$^-$ |
| 62 | | N-(2-Morpholin-4-ylethyl)-4-(2-oxo-4-trifluoromethyl-1,2-dihydroquinolin-6-ylmethyl)-benzenesulfonamide | 1.30 | 496.2 [M + H]$^+$ |

-continued

| Example | CHEMISTRY | Name | RT | Base Peak |
|---|---|---|---|---|
| 63 | | N-(3-Dimethylamino-2,2-dimethylpropyl)-4-(2-oxo-4-trifluoromethyl-1,2-dihydroquinolin-6-ylmethyl)-benzenesulfonamide | 1.30 | 496.2 [M + H]$^+$ |
| 64 | | N-(1-Methyl-1-phenylethyl)-4-(2-oxo-4-trifluoromethyl-1,2-dihydroquinolin-6-ylmethyl)-benzenesulfonamide | 1.88 | 499.2 [M − H]$^-$ |
| 65 | | 4-(2-Oxo-4-trifluoromethyl-1,2-dihydroquinolin-6-ylmethyl)-N-(2-phenylpropyl)-benzenesulfonamide | 1.94 | 499.2 [M − H]$^-$ |

-continued

| Example | CHEMISTRY | Name | RT | Base Peak |
|---|---|---|---|---|
| 66 | | N-(3-Methoxybenzyl)-4-(2-oxo-4-trifluoromethyl-1,2-dihydroquinolin-6-ylmethyl)-benzenesulfonamide | 1.85 | 501.2 [M − H]− |
| 67 | | N-(5-Fluoro-2-methylbenzyl)-4-(2-oxo-4-trifluoromethyl-1,2-dihydroquinolin-6-ylmethyl)-benzenesulfonamide | 1.91 | 503.2 [M − H]− |
| 68 | | N-[3-(2-Oxopyrrolidin-1-yl)propyl]-4-(2-oxo-4-trifluoromethyl-1,2-dihydroquinolin-6-ylmethyl)-benzenesulfonamide | 1.58 | 508.2 [M + H]+ |

-continued

| Example | CHEMISTRY | Name | RT | Base Peak |
|---|---|---|---|---|
| 69 | | N-(2,6-Difluorobenzyl)-4-(2-oxo-4-trifluoromethyl-1,2-dihydroquinolin-6-ylmethyl)-benzenesulfonamide | 1.80 | 507.2 [M − H]− |
| 70 | | 4-(2-Oxo-4-trifluoromethyl-1,2-dihydroquinolin-6-ylmethyl)-N-(4-phenylbutyl)-benzenesulfonamide | 1.97 | 513.2 [M − H]− |
| 71 | | N-(2-Ethoxybenzyl)-4-(2-oxo-4-trifluoromethyl-1,2-dihydroquinolino-6-ylmethyl)-benzenesulfonamide | 1.94 | 515.2 [M − H]− |

-continued

| Example | CHEMISTRY | Name | RT | Base Peak |
|---|---|---|---|---|
| 72 | | N-(3-Hydroxy-1-phenylpropyl)-4-(2-oxo-4-trifluoromethyl-1,2-dihydroquinolin-6-ylmethyl)-benzenesulfonamide | 1.67 | 515.2 [M − H]⁻ |
| 73 | | N-(2-Methylsulfanylbenzyl)-4-(2-oxo-4-trifluoromethyl-1,2-dihydroquinolin-6-ylmethyl)-benzenesulfonamide | 1.90 | 517.2 [M − H]⁻ |
| 74 | | N-[2-(4-Chlorophenyl)ethyl]-4-(2-oxo-4-trifluoromethyl-1,2-dihydroquinolin-6-ylmethyl)-benzenesulfonamide | 1.95 | 519.2 [M − H]⁻ |
| 75 | | N-[3-(4-Methylpiperazin-1-yl)propyl]-4-(2-oxo-4-trifluoromethyl-1,2-dihydroquinolin-6-ylmethyl)-benzenesulfonamide | 1.24 | 523.3 [M + H]⁺ |

-continued

| Example | CHEMISTRY | Name | RT | Base Peak |
|---|---|---|---|---|
| 76 | | N-(5-Chloro-2-fluorobenzyl)-4-(2-oxo-4-trifluoromethyl-1,2-dihydroquinolin-6-ylmethyl)-benzenesulfonamide | 1.89 | 523.1 [M − H]⁻ |
| 77 | | N-(3-Chloro-2-fluorobenzyl)-4-(2-oxo-4-trifluoromethyl-1,2-dihydroquinolin-6-ylmethyl)-benzenesulfonamide | 1.88 | 523.1 [M − H]⁻ |
| 78 | | N-(2-Chloro-6-fluorobenzyl)-4-(2-oxo-4-trifluoromethyl-1,2-dihydroquinolin-6-ylmethyl)-benzenesulfonamide | 1.88 | 523.1 [M − H]⁻ |

-continued

| Example | CHEMISTRY | Name | RT | Base Peak |
|---|---|---|---|---|
| 79 | 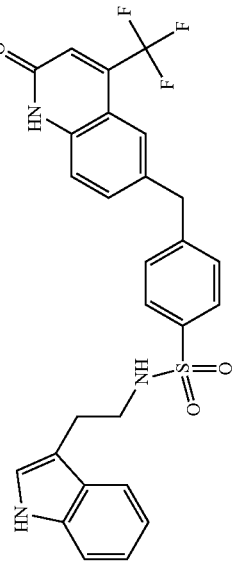 | N-[2-(1H-Indol-3-yl)ethyl]-4-(2-oxo-4-trifluoromethyl-1,2-dihydroquinolin-6-ylmethyl)-benzenesulfonamide | 1.82 | 524.2 [M − H]⁻ |
| 80 | 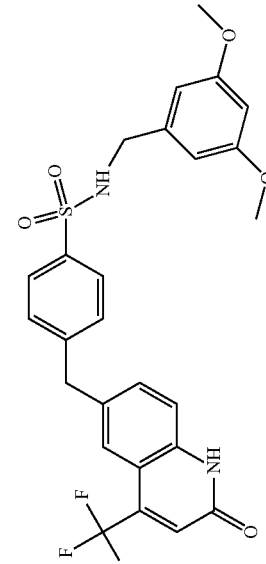 | N-(3,5-Dimethoxybenzyl)-4-(2-oxo-4-trifluoromethyl-1,2-dihydroquinolin-6-ylmethyl)-benzenesulfonamide | 1.84 | 531.2 [M − H]⁻ |
| 81 | 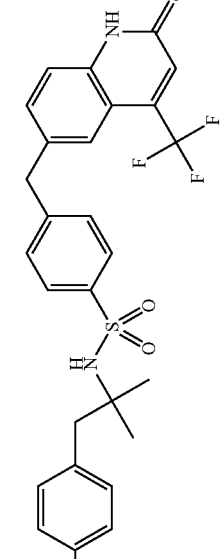 | N-[2-(4-Fluorophenyl)-1,1-dimethylethyl]-4-(2-oxo-4-trifluoromethyl-1,2-dihydroquinolin-6-ylmethyl)-benzenesulfonamide | 2.02 | 531.2 [M − H]⁻ |
| 82 | 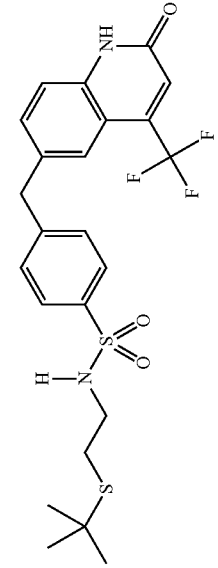 | N-(2-tert-Butylsulfanylethyl)-4-(2-oxo-4-trifluoromethyl-1,2-dihydroquinolin-6-ylmethyl)-benzenesulfonamide | 1.93 | 497.2 [M − H]⁻ |

-continued

| Example | CHEMISTRY | Name | RT | Base Peak |
|---|---|---|---|---|
| 83 | | N-(2-Difluoromethoxybenzyl)-4-(2-oxo-4-trifluoromethyl-1,2-dihydroquinolin-6-ylmethyl)-benzenesulfonamide | 1.87 | 537.1 [M − H]− |
| 84 | | N-(2-Chloro-6-fluoro-3-methylbenzyl)-4-(2-oxo-4-trifluoromethyl-1,2-dihydroquinolin-6-ylmethyl)-benzenesulfonamide | 1.94 | 537.1 [M − H]− |
| 85 | | N-(2,4-Dichlorobenzyl)-4-(2-oxo-4-trifluoromethyl-1,2-dihydroquinolin-6-ylmethyl)-benzenesulfonamide | 1.99 | 539.1 [M − H]− |

| Example | CHEMISTRY | Name | RT | Base Peak |
|---|---|---|---|---|
| 86 | | N-(1-Benzylpyrrolidin-3-yl)-4-(2-oxo-4-trifluoromethyl-1,2-dihydroquinolin-6-ylmethyl)-benzenesulfonamide | 1.38 | 542.2 [M + H]+ |
| 87 | | N-(2-Chloro-3,6-difluorobenzyl)-4-(2-oxo-4-trifluoromethyl-1,2-dihydroquinolin-6-ylmethyl)-benzenesulfonamide | 1.89 | 541.1 [M − H]− |
| 88 | | N-(3-Hydroxymethyl-bicyclo[2.2.1]hept-2-yl)-4-(2-oxo-4-trifluoromethyl-1,2-dihydroquinolin-6-ylmethyl)-benzenesulfonamide | 1.69 | 505.2 [M − H]− |

-continued

| Example | CHEMISTRY | Name | RT | Base Peak |
|---|---|---|---|---|
| 89 | | [4-(2-Oxo-4-trifluoromethyl-1,2-dihydroquinolin-6-ylmethyl)-benzenesulfonylamino]-phenylacetic acid ethyl ester | 1.90 | 543.2 [M − H]⁻ |
| 90 | | N-(2-Fluoro-5-trifluoromethylbenzyl)-4-(2-oxo-4-trifluoromethyl-1,2-dihydroquinolin-6-ylmethyl)-benzenesulfonamide | 1.95 | 557.2 [M − H]⁻ |
| 91 | | 3-[4-(2-Oxo-4-trifluoromethyl-1,2-dihydroquinolin-6-ylmethyl)-benzenesulfonylamino]-3-phenylpropionic acid ethyl ester | 1.85 | 557.2 [M − H]⁻ |

-continued

| Example | CHEMISTRY | Name | RT | Base Peak |
|---|---|---|---|---|
| 92 | | N-(2,2-Diphenylethyl)-4-(2-oxo-4-trifluoromethyl-1,2-dihydroquinolin-6-ylmethyl)-benzenesulfonamide | 2.03 | 561.2 [M − H]⁻ |
| 93 | | N-(2-Benzyloxycyclohexyl)-4-(2-oxo-4-trifluoromethyl-1,2-dihydroquinolin-6-ylmethyl)-benzenesulfonamide | 2.04 | 571.2 [M + H]⁺ |
| 94 | | N-[2-(2-Hydroxymethyl-phenylsulfanyl)benzyl]-4-(2-oxo-4-trifluoromethyl-1,2-dihydroquinolin-6-ylmethyl)-benzenesulfonamide | 1.89 | 609.2 [M − H]⁻ |

-continued

| Example | CHEMISTRY | Name | RT | Base Peak |
|---|---|---|---|---|
| 95 | | N-Cyclohexyl-N-(2-hydroxyethyl)-4-(2-oxo-4-trifluoromethyl-2H-chromen-6-ylmethyl)benzenesulfonamide | 1.99 | 510.2 [M + H]$^+$ |
| 96 | | N-Methyl-N-(1-methylpipendin-4-yl)-4-(2-oxo-4-trifluoromethyl-2H-chromen-6-ylmethyl)-benzenesulfonamide | 1.38 | 495.2 [M + H]$^+$ |
| 97 | | N,N-Dibutyl-4-(2-oxo-4-trifluoromethyl-2H-chromen-6-ylmethyl)benzenesulfonamide | 2.34 | 496.2 [M + H]$^+$ |
| 98 | | N-Ethyl-4-(2-oxo-4-trifluoromethyl-2H-chromen-6-ylmethyl)-N-pyridin-4-ylmethyl)-benzenesulfonamide | 1.52 | 503.2 [M + H]$^+$ |

-continued

| Example | CHEMISTRY | Name | RT | Base Peak |
|---|---|---|---|---|
| 99 | | N-Butyl-N-ethyl-4-(2-oxo-4-trifluoromethyl-2H-chromen-6-ylmethyl)benzenesulfonamide | 2.22 | 468.2 [M + H]+ |
| 100 | | N-Butyl-N-(2-hydroxyethyl)-4-(2-oxo-4-trifluoromethyl-2H-chromen-6-ylmethyl)-benzenesulfonamide | 1.96 | 528.2 [M + HCO$_2$]− |
| 101 | | N-Isopropyl-N-methyl-4-(2-oxo-4-trifluoromethyl-2H-chromen-6-ylmethyl)-benzenesulfonamide | 2.03 | 440.1 [M + H]+ |
| 102 | | N-(2-Hydroxyethyl)-4-(2-oxo-4-trifluoromethyl-2H-chromen-6-ylmethyl)-N-propylbenzenesulfonamide | 1.85 | 514.2 [M + HCO$_2$]− |

-continued

| Example | CHEMISTRY | Name | RT | Base Peak |
|---|---|---|---|---|
| 103 | | N-Benzyl-N-(2-hydroxyethyl)-4-(2-oxo-4-trifluoromethyl-2H-chromen-6-ylmethyl)-benzenesulfonamide | 1.99 | 518.2 [M + H]⁺ |
| 104 | | N-Cyclopropylmethyl-4-(2-oxo-4-trifluoromethyl-2H-chromen-6-ylmethyl)-N-propylbenzenesulfonamide | 2.20 | 480.2 [M + H]⁺ |
| 106 | | N-Cyclohexyl-N-methyl-4-(2-oxo-4-trifluoromethyl-2H-chromen-6-ylmethyl)-benzenesulfonamide | 2.22 | 480.2 [M + H]⁺ |
| 107 | | N-Butyl-N-methyl-4-(2-oxo-4-trifluoromethyl-2H-chromen-6-ylmethyl)benzenesulfonamide | 2.15 | 454.2 [M + H]⁺ |

-continued

| Example | CHEMISTRY | Name | RT | Base Peak |
|---|---|---|---|---|
| 108 | | N-(2-Cyanoethyl)-N-methyl-4-(2-oxo-4-trifluoromethyl-2H-chromen-6-ylmethyl)-benzenesulfonamide | 1.91 | 449.2 [M − H]− |
| 109 | | N,N-Dibenzyl-4-(2-oxo-4-trifluoromethyl-2H-chromen-6-ylmethyl)benzenesulfonamide | 2.35 | 564.2 [M + H]+ |
| 110 | | N-Benzyl-N-ethyl-4-(2-oxo-4-trifluoromethyl-2H-chromen-6-ylmethyl)benzenesulfonamide | 2.24 | 502.2 [M + H]+ |
| 111 | | N-Methyl-4-(2-oxo-4-trifluoromethyl-2H-chromen-6-ylmethyl)-N-(2-pyridin-2-ylethyl)benzenesulfonamide | 1.53 | 503.2 [M + H]+ |

| Example | CHEMISTRY | Name | RT | Base Peak |
|---|---|---|---|---|
| 112 | | N-Methyl-4-(2-oxo-4-trifluoromethyl-2H-chromen-6-ylmethyl)-N-phenethyl-benzenesulfonamide | 2.21 | 502.2 [M + H]+ |
| 113 | | 4-(2-Oxo-4-trifluoromethyl-2H-chromen-6-ylmethyl)-N-phenylbenzenesulfonamide | 1.99 | 458.1 [M − H]− |
| 114 | | N-Methyl-4-(2-oxo-4-trifluoromethyl-2H-chromen-6-ylmethyl)-N-phenylbenzenesulfonamide | 2.14 | 474.2 [M + H]+ |
| 115 | | 4-(2-Oxo-4-trifluoromethyl-2H-chromen-6-ylmethyl)-N-m-tolylbenzenesulfonamide | 2.04 | 472.2 [M − H]− |

| Example | CHEMISTRY | Name | RT | Base Peak |
|---|---|---|---|---|
| 116 | | 4-(2-Oxo-4-trifluoromethyl-2H-chromen-6-ylmethyl)-N-p-tolylbenzenesulfonamide | 2.08 | 472.1 [M − H]⁻ |
| 117 | | N-(4-Fluorophenyl)-4-(2-oxo-4-trifluoromethyl-2H-chromen-6-ylmethyl)benzenesulfonamide | 2.04 | 476.1 [M − H]⁻ |
| 118 | | N-(4-Ethynylphenyl)-4-(2-oxo-4-trifluoromethyl-2H-chromen-6-ylmethyl)-benzenesulfonamide | 2.06 | 482.1 [M − H]⁻ |
| 119 | | N-(3-Ethylphenyl)-4-(2-oxo-4-trifluoromethyl-2H-chromen-6-ylmethyl)-benzenesulfonamide | 2.14 | 486.2 [M − H]⁻ |

-continued

| Example | CHEMISTRY | Name | RT | Base Peak |
|---|---|---|---|---|
| 120 | | N-(4-Ethylphenyl)-4-(2-oxo-4-trifluoromethyl-2H-chromen-6-ylmethyl)-benzenesulfonamide | 2.11 | 486.2 [M − H]$^-$ |
| 121 | | N-(2-Hydroxymethylphenyl)-4-(2-oxo-4-trifluoromethyl-2H-chromen-6-ylmethyl)-benzenesulfonamide | 1.89 | 488.1 [M − H]$^-$ |
| 122 | | N-(3-Hydroxymethylphenyl)-4-(2-oxo-4-trifluoromethyl-2H-chromen-6-ylmethyl)-benzenesulfonamide | 1.82 | 488.1 [M − H]$^-$ |

-continued

| Example | CHEMISTRY | Name | RT | Base Peak |
|---|---|---|---|---|
| 123 | | N-(2-Methoxyphenyl)-4-(2-oxo-4-trifluoromethyl-2H-chromen-6-ylmethyl)-benzenesulfonamide | 2.05 | 488.2 [M − H]− |
| 124 | | N-(4-Hydroxymethylphenyl)-4-(2-oxo-4-trifluoromethyl-2H-chromen-6-ylmethyl)-benzenesulfonamide | 1.77 | 488.1 [M − H]− |
| 125 | | 4-(2-Oxo-4-trifluoromethyl-2H-chromen-6-ylmethyl)-N-quinolin-6-ylbenzenesulfonamide | 1.67 | 511.2 [M + H]+ |

| Example | CHEMISTRY | Name | RT | Base Peak |
|---|---|---|---|---|
| 126 |  | N-(4-Cyanomethylphenyl)-4-(2-oxo-4-trifluoromethyl-2H-chromen-6-ylmethyl)-benzenesulfonamide | 1.91 | 497.2 [M − H]⁻ |
| 127 | 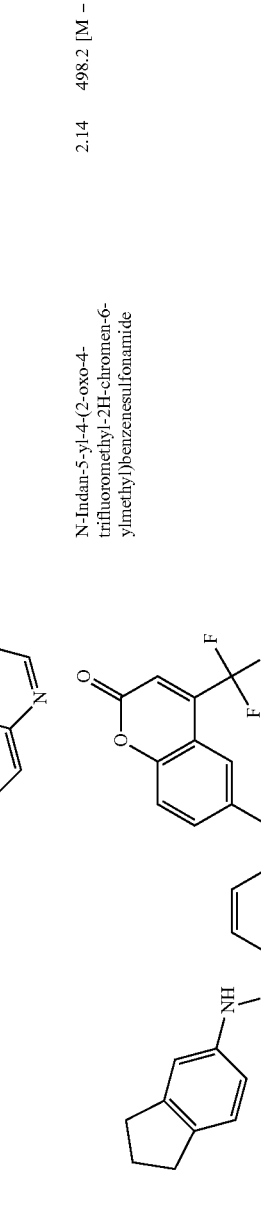 | N-Indan-5-yl-4-(2-oxo-4-trifluoromethyl-2H-chromen-6-ylmethyl)benzenesulfonamide | 2.14 | 498.2 [M − H]⁻ |
| 128 | 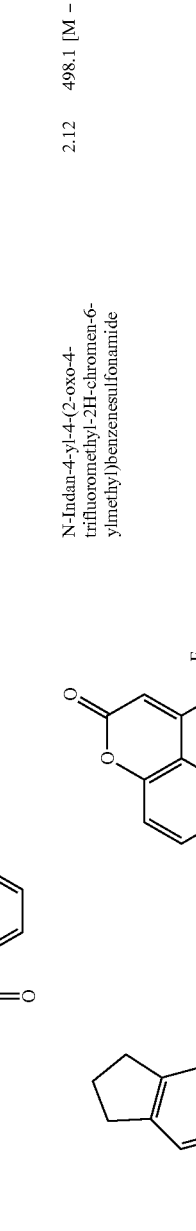 | N-Indan-4-yl-4-(2-oxo-4-trifluoromethyl-2H-chromen-6-ylmethyl)benzenesulfonamide | 2.12 | 498.1 [M − H]⁻ |

| Example | CHEMISTRY | Name | RT | Base Peak |
|---|---|---|---|---|
| 129 | | N-(3-Acetylphenyl)-4-(2-oxo-4-trifluoromethyl-2H-chromen-6-ylmethyl)benzenesulfonamide | 1.93 | 500.1 [M − H]⁻ |
| 130 | | N-(4-Isopropylphenyl)-4-(2-oxo-4-trifluoromethyl-2H-chromen-6-ylmethyl)-benzenesulfonamide | 2.20 | 500.2 [M − H]⁻ |
| 131 | | N-Benzo[1,3]dioxol-5-yl-4-(2-oxo-4-trifluoromethyl-2H-chromen-6-ylmethyl)-benzenesulfonamide | 1.99 | 502.1 [M − H]⁻ |

| Example | CHEMISTRY | Name | RT | Base Peak |
|---|---|---|---|---|
| 132 | | N-(4-Methylbiphenyl-3-yl)-4-(2-oxo-4-trifluoromethyl-2H-chromen-6-ylmethyl)-benzenesulfonamide | 2.23 | 548.2 [M − H]⁻ |
| 133 | | N-[3-(1-Hydroxyethyl)phenyl]-4-(2-oxo-4-trifluoromethyl-2H-chromen-6-ylmethyl)-benzenesulfonamide | 1.85 | 502.2 [M − H]⁻ |
| 134 | | N-(3-Methylsulfanylphenyl)-4-(2-oxo-4-trifluoromethyl-2H-chromen-6-ylmethyl)-benzenesulfonamide | 2.09 | 504.1 [M − H]⁻ |

| Example | CHEMISTRY | Name | RT | Base Peak |
|---|---|---|---|---|
| 135 | | N-(4-Chlorophenyl)-4-(2-oxo-4-trifluoromethyl-2H-chromen-6-ylmethyl)benzenesulfonamide | 2.09 | 492.1 [M − H]⁻ |
| 136 | | N-Isoquinolin-3-yl-4-(2-oxo-4-trifluoromethyl-2H-chromen-6-ylmethyl)benzenesulfonamide | 2.02 | 511.1 [M + H]⁺ |
| 137 | | 4-(2-Oxo-4-trifluoromethyl-2H-chromen-6-ylmethyl)-N-quinolin-8-ylbenzenesulfonamide | 2.12 | 511.1 [M + H]⁺ |

-continued

| Example | CHEMISTRY | Name | RT | Base Peak |
|---|---|---|---|---|
| 138 | 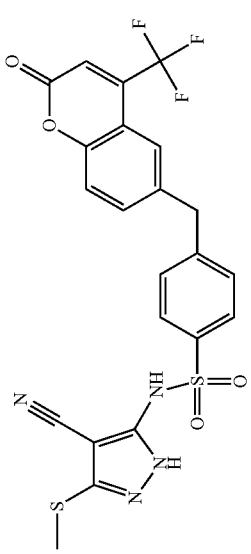 | N-(4-Cyano-5-methylsulfanyl-2H-pyrazol-3-yl)-4-(2-oxo-4-trifluoromethyl-2H-chromen-6-ylmethyl)benzenesulfonamide | 2.01 | 519.1 [M + H]$^+$ |
| 139 | 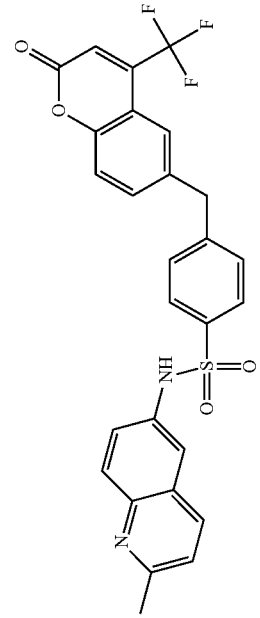 | N-(2-Methylquinolin-6-yl)-4-(2-oxo-4-trifluoromethyl-2H-chromen-6-ylmethyl)-benzenesulfonamide | 1.53 | 525.1 [M + H]$^+$ |
| 140 | 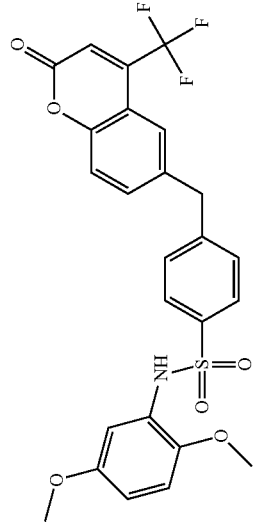 | N-(2,5-Dimethoxyphenyl)-4-(2-oxo-4-trifluoromethyl-2H-chromen-6-ylmethyl)-benzenesulfonamide | 2.03 | 518.1 [M − H]$^-$ |
| 141 | 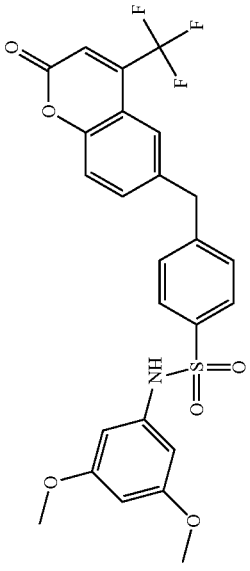 | N-(3,5-Dimethoxyphenyl)-4-(2-oxo-4-trifluoromethyl-2H-chromen-6-ylmethyl)-benzenesulfonamide | 2.02 | 518.2 [M − H]$^-$ |

-continued

| Example | CHEMISTRY | Name | RT | Base Peak |
|---|---|---|---|---|
| 142 | | N-(3-Isopropoxyphenyl)-4-(2-oxo-4-trifluoromethyl-2H-chromen-6-ylmethyl)-benzenesulfonamide | 2.14 | 516.2 [M − H]⁻ |
| 143 | | N-(3-Difluoromethoxyphenyl)-4-(2-oxo-4-trifluoromethyl-2H-chromen-6-ylmethyl)-benzenesulfonamide | 2.05 | 524.1 [M − H]⁻ |
| 144 | | N-(3-Oxazol-5-ylphenyl)-4-(2-oxo-4-trifluoromethyl-2H-chromen-6-ylmethyl)-benzenesulfonamide | 1.93 | 525.2 [M − H]⁻ |

| Example | CHEMISTRY | Name | RT | Base Peak |
|---|---|---|---|---|
| 145 | | 4-(2-Oxo-4-trifluoromethyl-2H-chromen-6-ylmethyl)-N-(3-trifluoromethylphenyl)-benzenesulfonamide | 2.13 | 526.1 [M − H]⁻ |
| 146 | | 4-(2-Oxo-4-trifluoromethyl-2H-chromen-6-ylmethyl)-N-(2-piperidin-1-ylphenyl)-benzenesulfonamide | 2.29 | 543.2 [M + H]⁺ |
| 147 | | 4-(2-Oxo-4-trifluoromethyl-2H-chromen-6-ylmethyl)-N-(3-trifluoromethoxyphenyl)-benzenesulfonamide | 2.17 | 542.1 [M − H]⁻ |
| 148 | | {4-[4-(2-Oxo-4-trifluoromethyl-2H-chromen-6-ylmethyl)-benzenesulfonylamino]-phenyl}acetic acid ethyl ester | 2.03 | 544.2 [M − H]⁻ |

-continued

| Example | CHEMISTRY | Name | RT | Base Peak |
|---|---|---|---|---|
| 149 | | N-(3-Benzylphenyl)-4-(2-oxo-4-trifluoromethyl-2H-chromen-6-ylmethyl)benzenesulfonamide | 2.19 | 548.2 [M − H]− |
| 150 | | N-(4-Ethoxyphenyl)-4-(2-oxo-4-trifluoromethyl-2H-chromen-6-ylmethyl)-benzenesulfonamide | 2.07 | 502.2 [M − H]− |
| 151 | | N-[4-(2-Hydroxyethyl)phenyl]-4-(2-oxo-4-trifluoromethyl-2H-chromen-6-ylmethyl)-benzenesulfonamide | 1.80 | 502.1 [M − H]− |
| 152 | | N-(3-Benzyloxyphenyl)-4-(2-oxo-4-trifluoromethyl-2H-chromen-6-ylmethyl)-benzenesulfonamide | 2.18 | 564.2 [M − H]− |

| Example | CHEMISTRY | Name | RT | Base Peak |
|---|---|---|---|---|
| 153 | | N-(3,5-Di-tert-butylphenyl)-4-(2-oxo-4-trifluoromethyl-2H-chromen-6-ylmethyl)-benzenesulfonamide | 2.40 | 570.3 [M − H]⁻ |
| 154 | | N-Benzyl-N-(4-methoxyphenyl)-4-(2-oxo-4-trifluoromethyl-2H-chromen-6-ylmethyl)benzenesulfonamide | 2.29 | 580.2 [M + H]⁺ |
| 155 | | 4-(2-Oxo-4-trifluoromethyl-2H-chromen-6-ylmethyl)-N-[4-(3-trifluoromethylpyrazol-1-yl)phenyl]benzenesulfonamide | 2.13 | 592.1 [M − H]⁻ |
| 156 | | N-(3-Methoxyphenyl)-4-(2-oxo-4-trifluoromethyl-2H-chromen-6-ylmethyl)benzene-sulfonamide | 2.02 | 488.2 [M − H]⁻ |

-continued

| Example | CHEMISTRY | Name | RT | Base Peak |
|---|---|---|---|---|
| 157 | | N-(1-Benzylpipendin-4-yl)-4-(2-oxo-4-trifluoromethyl-2H-chromen-6-ylmethyl)benzenesulfonamide | 1.43 | 557.2 [M + H]+ |
| 158 | | N-Cyclopentyl-4-(2-oxo-4-trifluoromethyl-2H-chromen-6-ylmethyl)benzenesulfonamide | 2.06 | 450.2 [M − H]− |
| 159 | | N-(3-Methylbutyl)-4-(2-oxo-4-trifluoromethyl-2H-chromen-6-ylmethyl)benzenesulfonamide | 2.09 | 452.2 [M − H]− |
| 160 | | N-(2,3-Dihydroxypropyl)-4-(2-oxo-4-trifluoromethyl-2H-chromen-6-ylmethyl)benzenesulfonamide | 1.61 | 456.1 [M − H]− |

-continued

| Example | CHEMISTRY | Name | RT | Base Peak |
|---|---|---|---|---|
| 161 | | N-(3,3-Dimethylbutyl)-4-(2-oxo-4-trifluoromethyl-2H-chromen-6-ylmethyl)benzenesulfonamide | 2.13 | 466.2 [M − H]⁻ |
| 162 | | N-Benzyl-4-(2-oxo-4-trifluoromethyl-2H-chromen-6-ylmethyl)benzenesulfonamide | 2.05 | 472.1 [M − H]⁻ |
| 163 | | 4-(2-Oxo-4-trifluoromethyl-2H-chromen-6-ylmethyl)-N-pyridin-3-ylmethylbenzenesulfonamide | 1.50 | 475.1 [M + H]⁺ |
| 164 | | N-(5-Methylfuran-2-ylmethyl)-4-(2-oxo-4-trifluoromethyl-2H-chromen-6-ylmethyl)benzenesulfonamide | 2.01 | 476.1 [M − H]⁻ |

-continued

| Example | CHEMISTRY | Name | RT | Base Peak |
|---|---|---|---|---|
| 165 | | N-Cyclohexylmethyl-4-(2-oxo-4-trifluoromethyl-2H-chromen-6-ylmethyl)benzene-sulfonamide | 2.17 | 478.2 [M − H]⁻ |
| 166 | | N-Cycloheptyl-4-(2-oxo-4-trifluoromethyl-2H-chromen-6-ylmethyl)benzenesulfonamide | 2.17 | 478.2 [M − H]⁻ |
| 167 | | N-(1-Hydroxymethyl-cyclopentyl)-4-(2-oxo-4-trifluoromethyl-2H-chromen-6-ylmethyl)benzenesulfonamide | 1.84 | 482.2 [M + H]⁺ |
| 168 | | 4-(2-Oxo-4-trifluoromethyl-2H-chromen-6-ylmethyl)-N-phenethylbenzenesulfonamide | 2.10 | 486.2 [M − H]⁻ |

-continued

| Example | CHEMISTRY | Name | RT | Base Peak |
|---|---|---|---|---|
| 169 | | N-(3-Methylbenzyl)-4-(2-oxo-4-trifluoromethyl-2H-chromen-6-ylmethyl)benzenesulfonamide | 2.08 | 486.2 [M − H]− |
| 170 | | N-(4-Methylbenzyl)-4-(2-oxo-4-trifluoromethyl-2H-chromen-6-ylmethyl)benzenesulfonamide | 2.12 | 486.2 [M − H]− |
| 171 | | N-(2-Methylbenzyl)-4-(2-oxo-4-trifluoromethyl-2H-chromen-6-ylmethyl)benzenesulfonamide | 2.10 | 486.2 [M − H]− |

| Example | CHEMISTRY | Name | RT | Base Peak |
|---|---|---|---|---|
| 172 | | 4-(2-Oxo-4-trifluoromethyl-2H-chromen-6-ylmethyl)-N-(1-phenylethyl)-benzenesulfonamide | 2.09 | 486.2 [M − H]− |
| 173 | | N-(4-Fluorobenzyl)-4-(2-oxo-4-trifluoromethyl-2H-chromen-6-ylmethyl)benzenesulfonamide | 2.08 | 490.1 [M − H]− |
| 174 | | N-(3-Imidazol-1-ylpropyl)-4-(2-oxo-4-trifluoromethyl-2H-chromen-6-ylmethyl)benzenesulfonamide | 1.34 | 492.2 [M + H]+ |

-continued

| Example | CHEMISTRY | Name | RT | Base Peak |
|---|---|---|---|---|
| 175 | | N-(2-Cyclohex-1-enylethyl)-4-(2-oxo-4-trifluoromethyl-2H-chromen-6-ylmethyl)benzenesulfonamide | 2.23 | 490.2 [M − H]− |
| 176 | | 4-(2-Oxo-4-trifluoromethyl-2H-chromen-6-ylmethyl)-N-(2-thiophen-2-ylethyl)benzenesulfonamide | 2.06 | 492.1 [M − H]− |
| 177 | | N-(2-Hydroxycyclohexylmethyl)-4-(2-oxo-4-trifluoromethyl-2H-chromen-6-ylmethyl)benzenesulfonamide | 1.90 | 496.2 [M + H]+ |
| 178 | | N-Indan-1-yl-4-(2-oxo-4-trifluoromethyl-2H-chromen-6-ylmethyl)benzenesulfonamide | 2.13 | 498.2 [M − H]− |

| Example | CHEMISTRY | Name | RT | Base Peak |
|---|---|---|---|---|
| 179 | | N-(1-Methyl-1-phenylethyl)-4-(2-oxo-4-trifluoromethyl-2H-chromen-6-ylmethyl)benzenesulfonamide | 2.13 | 500.2 [M − H]$^-$ |
| 180 | | 4-(2-Oxo-4-trifluoromethyl-2H-chromen-6-ylmethyl)-N-(2-phenylpropyl)-benzenesulfonamide | 2.12 | 500.2 [M − H]$^-$ |
| 181 | | 4-(2-Oxo-4-trifluoromethyl-2H-chromen-6-ylmethyl)-N-(2-phenoxyethyl)-benzenesulfonamide | 2.09 | 502.2 [M − H]$^-$ |

| Example | CHEMISTRY | Name | RT | Base Peak |
|---|---|---|---|---|
| 182 | | N-(4-Methoxybenzyl)-4-(2-oxo-4-trifluoromethyl-2H-chromen-6-ylmethyl)-benzenesulfonamide | 2.03 | 502.2 [M − H]⁻ |
| 183 | | N-(3-Methoxybenzyl)-4-(2-oxo-4-trifluoromethyl-2H-chromen-6-ylmethyl)-benzenesulfonamide | 2.06 | 502.2 [M − H]⁻ |
| 184 | | N-(2-Hydroxy-1-phenylethyl)-4-(2-oxo-4-trifluoromethyl-2H-chromen-6-ylmethyl)-benzenesulfonamide | 1.83 | 502.2 [M − H]⁻ |

| Example | CHEMISTRY | Name | RT | Base Peak |
|---|---|---|---|---|
| 185 | 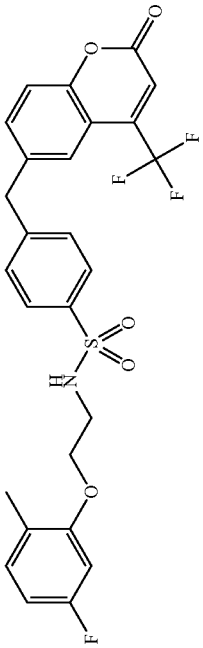 | N-(5-Fluoro-2-methylbenzyl)-4-(2-oxo-4-trifluoromethyl-2H-chromen-6-ylmethyl)-benzenesulfonamide | 2.11 | 504.2 [M − H]⁻ |
| 186 | 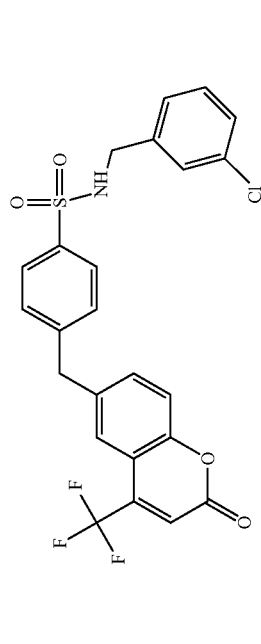 | N-(3-Chlorobenzyl)-4-(2-oxo-4-trifluoromethyl-2H-chromen-6-ylmethyl)benzenesulfonamide | 2.14 | 506.1 [M − H]⁻ |
| 187 | 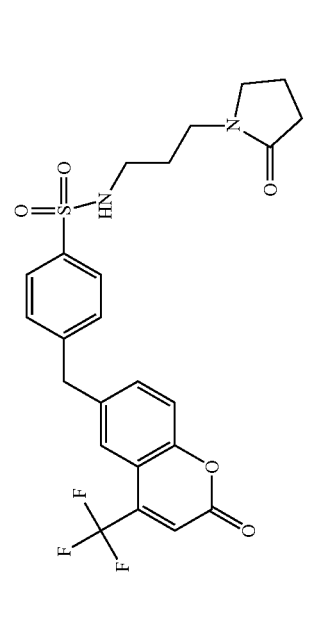 | N-[3-(2-Oxopyrrolidin-1-yl)propyl]-4-(2-oxo-4-trifluoromethyl-2H-chromen-6-ylmethyl)benzenesulfonamide | 1.73 | 509.2 [M + H]⁺ |
| 188 | 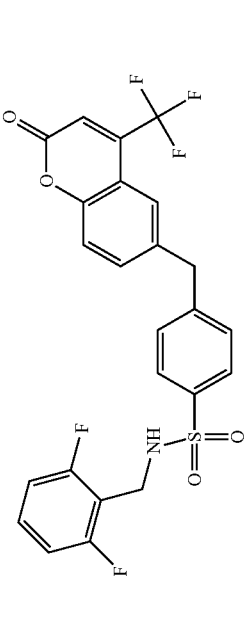 | N-(2,6-Difluorobenzyl)-4-(2-oxo-4-trifluoromethyl-2H-chromen-6-ylmethyl)benzenesulfonamide | 2.05 | 508.1 [M − H]⁻ |

-continued

| Example | CHEMISTRY | Name | RT | Base Peak |
|---|---|---|---|---|
| 189 | | N-(2,3-Dihydrobenzofuran-5-ylmethyl)-4-(2-oxo-4-trifluoromethyl-2H-chromen-6-ylmethyl)benzenesulfonamide | 2.02 | 514.2 [M − H]− |
| 190 | | N-[2-(2-Methoxyphenyl)ethyl]-4-(2-oxo-4-trifluoromethyl-2H-chromen-6-ylmethyl)benzenesulfonamide | 2.13 | 518.2 [M + H]+ |
| 191 | | N-(2-Ethoxybenzyl)-4-(2-oxo-4-trifluoromethyl-2H-chromen-6-ylmethyl)benzene-sulfonamide | 2.12 | 516.2 [M − H]− |

| Example | CHEMISTRY | Name | RT | Base Peak |
|---|---|---|---|---|
| 192 | | N-(3-Hydroxy-1-phenyl)propyl)-4-(2-oxo-4-trifluoromethyl-2H-chromen-6-ylmethyl)benzenesulfonamide | 1.88 | 516.2 [M − H]⁻ |
| 193 | | N-(4-Hydroxycyclohexyl)-4-(2-oxo-4-trifluoromethyl-2H-chromen-6-ylmethyl)benzenesulfonamide | 1.69 | 480.2 [M − H]⁻ |
| 194 | | N-(2-Methylsulfanylbenzyl)-4-(2-oxo-4-trifluoromethyl-2H-chromen-6-ylmethyl)benzenesulfonamide | 2.07 | 581.2 [M − H]⁻ |
| 195 | | N-[2-(4-Chlorophenyl)ethyl]-4-(2-oxo-4-trifluoromethyl-2H-chromen-6-ylmethyl)benzenesulfonamide | 2.16 | 520.1 [M − H]⁻ |

| Example | CHEMISTRY | Name | RT | Base Peak |
|---|---|---|---|---|
| 196 | | N-(2-Chloro-6-methylbenzyl)-4-(2-oxo-4-trifluoromethyl-2H-chromen-6-ylmethyl)benzenesulfonamide | 2.18 | 520.1 [M − H]− |
| 197 | | N-(2,3-Difluoro-4-methylbenzyl)-4-(2-oxo-4-trifluoromethyl-2H-chromen-6-ylmethyl)benzenesulfonamide | 2.13 | 522.1 [M − H]− |
| 198 | | N-[2-Chloro-4-fluorobenzyl-4-(2-oxo-4-trifluoromethyl-2H-chromen-6-ylmethyl)benzenesulfonamide | 2.15 | 524.1 [M − H]− |

-continued

| Example | CHEMISTRY | Name | RT | Base Peak |
|---|---|---|---|---|
| 199 | | N-(2-Difluoromethoxybenzyl)-4-(2-oxo-4-trifluoromethyl-2H-chromen-6-ylmethyl)benzenesulfonamide | 2.09 | 538.1 [M − H]⁻ |
| 200 | | N-(2-Chloro-6-fluoro-3-methylbenzyl)-4-(2-oxo-4-trifluoromethyl-2H-chromen-6-ylmethyl)benzenesulfonamide | 2.18 | 538.1 [M − H]⁻ |
| 201 | | 4-(2-Oxo-4-trifluoromethyl-2H-chromen-6-ylmethyl)-N-(2-trifluoromethylbenzyl)-benzenesulfonamide | 2.14 | 540.1 [M − H]⁻ |

-continued

| Example | CHEMISTRY | Name | RT | Base Peak |
|---|---|---|---|---|
| 202 | | N-(2-Chloro-3,6-difluorobenzyl)-4-(2-oxo-4-trifluoromethyl-2H-chromen-6-ylmethyl)benzenesulfonamide | 2.12 | 542.1 [M − H]⁻ |
| 203 | | N-(2-Bromobenzyl)-4-(2-oxo-4-trifluoromethyl-2H-chromen-6-ylmethyl)benzenesulfonamide | 2.16 | 550.1 [M − H]⁻ |
| 204 | | N-(2-Fluoro-5-trifluoromethylbenzyl)-4-(2-oxo-4-trifluoromethyl-2H-chromen-6-ylmethyl)benzene-sulfonamide | 2.15 | 558.1 [M − H]⁻ |
| 205 | | 3-[4-(2-Oxo-4-trifluoromethyl-2H-chromen-6-ylmethyl)-benzenesulfonylamino]-3-phenylpropionic acid ethyl ester | 2.12 | 558.2 [M − H]⁻ |

-continued

| Example | CHEMISTRY | Name | RT | Base Peak |
|---|---|---|---|---|
| 206 | | N-(2,2-Diphenylethyl)-4-(2-oxo-4-trifluoromethyl-2H-chromen-6-ylmethyl)benzene-sulfonamide | 2.23 | 562.2 [M − H]− |
| 207 | | N-(4-Bromo-2-fluorobenzyl)-4-(2-oxo-4-trifluoromethyl-2H-chromen-6-ylmethyl)benzenesulfonamide | 2.18 | 568.0 [M − H]− |
| 208 | | N-(2-Benzyloxycyclohexyl)-4-(2-oxo-4-trifluoromethyl-2H-chromen-6-ylmethyl)benzenesulfonamide | 2.25 | 570.2 [M − H]− |

-continued
| Example | CHEMISTRY | Name | RT | Base Peak |
|---|---|---|---|---|
| 209 | 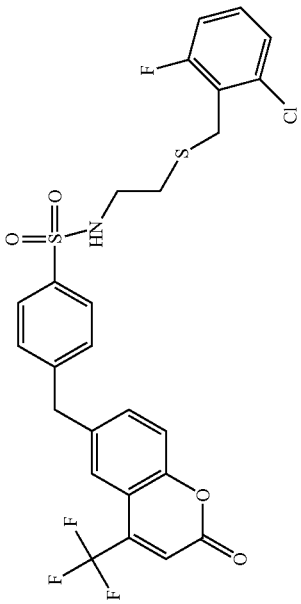 | N-[2-(2-Chloro-6-fluorobenzylsulfanyl)ethyl]-4-(2-oxo-4-trifluoromethyl-2H-chromen-6-ylmethyl)benzenesulfonamide | 2.22 | 584.1 [M − H]⁻ |

Example 57

Biological Data

The compounds ability to antagonize the effects of androgen on the androgen receptor were determined in the protocol described immediately below. The results are shown in Table 3.

Experimental Procedure for AR Antagonist Cell Assay

Cell line: MDA-MB453-MMTV clone 54–19. This cell line is a stable transfected cell line with MDA-MB453 cell background (human breast tumor cell expressing high level of androgen receptor). A MMTV minimal promoter containing ARE was first cloned in front of a firefly luciferase reporter gene. Then the cascade was cloned into transfection vector pUV120puro. Electroporation method was used for transfecting MDA-MB-453 cell. Puromycin resistant stable cell line was selected.

Cell Culture Media and Reagents:

Culture medium: DMEM (high glucose, Gibco cat #: 11960-044), 10% FBS, and 1% L-glutamine Plating medium: DMEM (phenol red free), 10% charcoal treated HyClone serum, 1% L-glutamine Assay medium: DMEM (phenol red free), 1% charcoal treated HyClone serum, 1% L-glutamine, and 1% penicillin/streptomycin 3× luciferase buffer: 2% beta-mercaptoethanol, 0.6% ATP, 0.0135% luciferine in cell lysis buffer Assay Procedure:
1. Cells are maintained in culture medium, splitting cells when they reach 80–90% confluence
2. To test compounds, 10,000 cells/well are plated to opaque 96 cell culture plate in 100 ul/well plating medium, culture for overnight at 37° C. in cell culture incubator
3. Carefully remove plating medium, then add 80 ul/well of pre-warmed assay medium, add 10 ul/well testing compound (final concentration at 10 uM or 1 uM), incubate at 37° C. for 30 minutes
4. Add 10 ul/well freshly prepared DHT (final concentration at 100 pM) to each well, incubate at 37° C. for 17 hr (overnight)
5. Add 50 ul/well 3× luciferase buffer, incubate at room temperature for 5 minutes, then count on Luminometer.

The fold induction over background by 100 pM DHT in the absence of testing compounds is standardized as 100% and experimental result is expressed as percentage of inhibition by testing compounds.

| IC50 (uM) | Example# |
|---|---|
| 2.8 | 15 |
| 2.02 | 16 |
| >10 | 17 |
| 3.16 | 18 |
| >10 | 19 |
| >10 | 20 |
| 9.09 | 21 |
| >10 | 22 |
| 1.67 | 23 |
| 10 | 24 |
| 1.12 | 25 |
| 1.97 | 26 |
| >10 | 27 |
| 10 | 28 |
| >10 | 29 |
| >10 | 30 |

-continued

| IC50 (uM) | Example# |
|---|---|
| >10 | 31 |
| 8.02 | 32 |
| >10 | 33 |
| >10 | 34 |
| >10 | 35 |
| 6.14 | 36 |
| >10 | 37 |
| >10 | 38 |
| >10 | 39 |
| 5.61 | 40 |
| >10 | 41 |
| >10 | 42 |
| >10 | 43 |
| 2.8 | 44 |
| >10 | 45 |
| >10 | 46 |
| >10 | 47 |
| 4.97 | 48 |
| >10 | 49 |
| >10 | 50 |
| 2.18 | 51 |
| 9.9 | 52 |
| >10 | 53 |
| >10 | 54 |
| >10 | 55 |
| 3.64 | 56 |
| >10 | 57 |
| >10 | 58 |
| 9.25 | 59 |
| 9.16 | 60 |
| N/A | 61 |
| 6.66 | 62 |
| 10 | 63 |
| N/A | 64 |
| 5.38 | 65 |
| N/A | 66 |
| 8.23 | 67 |
| 7.62 | 68 |
| 10 | 69 |
| >10 | 70 |
| >10 | 71 |
| >10 | 72 |
| >10 | 73 |
| >10 | 74 |
| 6.7 | 75 |
| >10 | 76 |
| >10 | 77 |
| >10 | 78 |
| 10.35 | 79 |
| >10 | 80 |
| 10 | 81 |
| >10 | 82 |
| >10 | 83 |
| >10 | 84 |
| ≈10 | 85 |
| 2.28 | 86 |
| >10 | 87 |
| >10 | 88 |
| >10 | 89 |
| 2.62 | 90 |
| >10 | 91 |
| 2.71 | 92 |
| >10 | 93 |
| >10 | 94 |
| >10 | 4 |
| >10 | 5 |
| >10 | 6 |
| >10 | 7 |
| 3.25 | 8 |
| >10 | 9 |
| 6.29 | 9A |
| >10 | 9B |
| >10 | 10 |
| >10 | 11 |
| >10 | 12 |
| >10 | 13 |
| 10 | 14 |

-continued

| IC50 (uM) | Example# |
|---|---|
| 0.72 | 113 |
| 5.94 | 114 |
| 2.05 | 115 |
| 1.21 | 116 |
| 3.46 | 117 |
| 5.47 | 118 |
| 3.42 | 119 |
| 1.32 | 120 |
| 3.17 | 121 |
| 1.83 | 122 |
| 4.08 | 123 |
| 2.31 | 124 |
| >10 | 125 |
| 1.89 | 126 |
| 2.77 | 127 |
| 4.77 | 128 |
| 2.16 | 129 |
| 3.91 | 130 |
| 2.4 | 131 |
| 8.13 | 132 |
| 6.91 | 133 |
| 1.24 | 134 |
| 2.01 | 135 |
| >10 | 136 |
| 7.08 | 137 |
| 1.9 | 138 |
| 2.03 | 139 |
| 7.3 | 140 |
| 3.24 | 141 |
| ≈10 | 142 |
| 2.81 | 143 |
| 2.17 | 144 |
| 1.72 | 145 |
| 4.82 | 146 |
| 8.58 | 147 |
| 3.13 | 148 |
| 4.74 | 149 |
| 7.2 | 150 |
| 1.75 | 151 |
| 0.77 | 152 |
| >10 | 153 |
| 6.06 | 154 |
| 6.5 | 155 |
| 1.72 | 156 |
| 1.03 | 95 |
| >10 | 96 |
| 6.23 | 97 |
| 2.43 | 98 |
| 4.15 | 99 |
| ≈10 | 100 |
| 2.65 | 101 |
| 2.91 | 102 |
| ≈10 | 103 |
| 1.79 | 104 |
| 3.52 | 105 |
| >10 | 106 |
| 3.45 | 107 |
| 4.72 | 108 |
| 8.26 | 109 |
| 5.94 | 110 |
| 4.78 | 111 |
| >10 | 112 |
| 6.09 | 157 |
| 6.5 | 158 |
| >10 | 159 |
| >10 | 160 |
| 10 | 161 |
| 10 | 162 |
| 3.08 | 163 |
| 10 | 164 |
| ≈10 | 165 |
| 6.97 | 166 |
| >10 | 167 |
| 10 | 168 |
| 5.81 | 169 |
| 10 | 170 |
| 9.62 | 171 |

-continued

| IC50 (uM) | Example# |
|---|---|
| 4.66 | 172 |
| 7.68 | 173 |
| 5.5 | 174 |
| 8.5 | 175 |
| 6 | 176 |
| 5.77 | 177 |
| 7.74 | 178 |
| >10 | 179 |
| 2.06 | 180 |
| 6.96 | 181 |
| 7.34 | 182 |
| 1.29 | 183 |
| 10 | 184 |
| 4.06 | 185 |
| >10 | 186 |
| 3.44 | 187 |
| 1.91 | 188 |
| 2.51 | 189 |
| 5.41 | 190 |
| 10 | 191 |
| 6.52 | 192 |
| 9.11 | 193 |
| 8 | 194 |
| 10 | 195 |
| 10 | 196 |
| 1.94 | 197 |
| 5.93 | 198 |
| 4.73 | 199 |
| 6.91 | 200 |
| 4.04 | 201 |
| 4.42 | 202 |
| 2.19 | 203 |
| >10 | 204 |
| 3.43 | 205 |
| 5.74 | 206 |
| 10 | 207 |
| 10 | 208 |
| 10 | 209 |

What is claimed is:
1. A compound of the formula

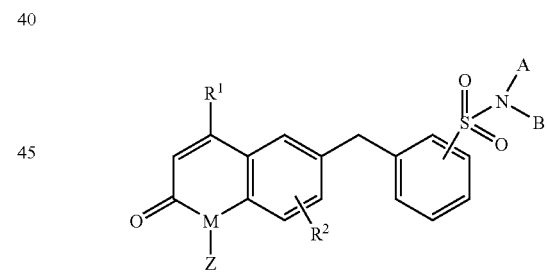

in which:
a. M is NZ or O;
b. Z is represented by H or $C_1$–$C_4$ alkyl;
c. $R^1$ is represented by —$CF_3$;
d. $R^2$ is absent, or may represent up to 2 substituents selected from the group consisting of halogen, nitrile, hydroxy, ($C_1$–$C_4$)alkyl, ($C_2$–$C_4$)alkenyl, ($C_2$–$C_4$)alkynyl, ($C_1$–$C_4$)alkoxy, ($C_1$–$C_2$)alkyl substituted with 1 or more halogens, ($C_1$–$C_2$)alkoxy substituted with one or more halogens, $SR^4$, and $NR^4R^5$;
e. $R^4$ is represented by hydrogen, ($C_1$–$C_4$)alkyl, optionally substituted phenyl, or optionally substituted benzyl;
f. $R^5$ is represented by hydrogen, ($C_1$–$C_4$)alkyl, optionally substituted phenyl, optionally substituted benzyl, optionally substituted heteroaryl, or optionally substituted heterocyclic;

g. A and B are each independently represented by a substituent selected from the group consisting of hydrogen, $(C_1-C_6)$alkyl, $(C_2-C_6)$alkenyl, $(C_2-C_6)$alkynyl, $(C_1-C_4)$alkanol, optionally substituted $(C_3-C_8)$cycloalkyl, optionally substituted $(C_5-C_8)$cycloalkenyl, optionally substituted phenyl, optionally substituted cycloalkylphenyl, optionally substituted heterocyclic, optionally substituted heteroaryl, $(C_1-C_6)$alkyl$R^6$, —$(CH^2)_m$—$R^7$—Y[—$CH_2]_n$—X—$R^8$ and, —$(CH_2)_q$CHX$^1$X$^2$;

h. $R^6$ is represented by a substituent selected from the group consisting of nitrile, OH, optionally substituted phenyl, optionally substituted cyloalkylphenyl, optionally substituted heterocyclic, optionally substituted heteroaryl, optionally substituted $(C_3-C_8)$cycloalkyl, optionally substituted $(C_5-C_8)$cycloalkenyl, SR$^4$, and NR$^4$R$^5$;

i. $R^7$ is absent, or is represented by a substituent selected from the group consisting of optionally substituted $(C_3-C_8)$cycloalkyl, optionally substituted $(C_5-C_8)$cycloalkenyl, optionally substituted heteroaryl, optionally substituted heterocyclic, and optionally substituted phenyl;

j. $R^8$ is absent, or is represented by a substituent selected from the group consisting of $(C_1-C_6)$alkyl, optionally substituted $(C_3-C_8)$cycloalkyl, optionally substituted $(C_5-C_8)$cycloalkenyl, optionally substituted heteroaryl, optionally substituted heterocyclic, optionally substituted phenyl, and optionally substituted cycloalkylphenyl;

k. m is an integer selected from 0, 1, 2, 3, or 4;

l. Y is absent, or is represented by O, C(O), C(O)O, CH$_2$C(O)O, OH, SH, S, or NR$^4$;

m. n is represented by an integer selected from 0, 1, 2, 3, or 4;

n. X is absent, or is represented by O, C(O), C(O)O, —CH$_2$C(O)O, OH, SH, S, or NR$^4$;

o. q is represented by an integer selected from 0, 1, 2, 3, or 4;

p. X$^1$ is represented by a substituent selected from the group consisting of hydroxy, nitrile, $(C_1-C_6)$alkyl, $(C_2-C_6)$alkenyl, $(C_2-C_6)$alkynyl, $(C_1-C_4)$alkanol, $(C_1-C_2)$alkyl substituted with 1 or more halogens, $(C_1-C_2)$alkoxy substituted with one or more halogens, optionally substituted $(C_3-C_8)$cycloalkyl, optionally substituted $(C_5-C_8)$cycloalkenyl, optionally substituted heteroaryl, optionally substituted heterocyclic, optionally substituted phenyl, and optionally substituted cycloalkylphenyl;

q. X$^2$ is represented by a substituent selected from the group consisting of $(C_3-C_8)$cycloalkyl, optionally substituted $(C_5-C_8)$cycloalkenyl, optionally substituted heteroaryl, optionally substituted heterocyclic, optionally substituted phenyl, optionally substituted cycloalkylphenyl, —CH$_2$C(O)OR$^4$ or;

r. a pharmaceutically acceptable salt, or solvate, thereof.

2. The compound according to claim 1 in which M is NZ and Z is hydrogen.

3. A pharmaceutical composition comprising a compound according to claim 1 in admixture with 1, or more, pharmaceutically acceptable excipients.

4. A topical pharmaceutical formulation comprising a compound according to claim 1 in admixture with 1, or more, pharmaceutically acceptable excipients suitable for dermal application.

5. A kit comprising a compound according to claim 1 packaged for retail distribution which advises a consumer how to utilize the compound to alleviate a condition selected from the group consisting of acne, alopecia, and oily skin.

6. A compound according to claim 1 selected from the group consisting of:
N-Isopropyl-4-(2-oxo-4-trifluoromethyl-1,2-dihydroquinolin-6-ylmethyl)benzenesulfonamide;
N-Butyl-4-(2-oxo-4-trifluoromethyl-1,2-dihydroquinolin-6-ylmethyl)benzenesulfonamide;
N-Benzyl-4-(2-oxo-4-trifluoromethyl-1,2-dihydroquinolin-6-ylmethyl)benzenesulfonamide;
N-Cyclohexyl-N-(2-hydroxyethyl)-4-(2-oxo-4-trifluoromethyl-1,2-dihydroquinolin-6-ylmethyl)benzenesulfonamide;
N-Ethyl-4-(2-oxo-4-trifluoromethyl-1,2-dihydroquinolin-6-ylmethyl)-N-pyridin-4-ylmethylbenzenesulfonamide;
N-Butyl-N-ethyl-4-(2-oxo-4-trifluoromethyl-1,2-dihydroquinolin-6-ylmethyl)benzenesulfonamide;
N-Isopropyl-N-methyl-4-(2-oxo-4-trifluoromethyl-1,2-dihydroquinolin-6-ylmethyl)benzenesulfonamide;
N-(2-Hydroxyethyl)-4-(2-oxo-4-trifluoromethyl-1,2-dihydroquinolin-6-ylmethyl)-N-propylbenzenesulfonamide;
N-Benzyl-N-(2-hydroxyethyl)-4-(2-oxo-4-trifluoromethyl-1,2-dihydroquinolin-6-ylmethyl)benzenesulfonamide;
N-Cyclopropylmethyl4-(2-oxo-4-trifluoromethyl-1,2-dihydroquinolin-6-ylmethyl)-N-propylbenzenesulfonamide;
N-Butyl-N-methyl-4-(2-oxo-4-trifluoromethyl-1,2-dihydroquinolin-6-ylmethyl)benzenesulfonamide;
N-(2-Cyanoethyl)-N-methyl4-(2-oxo-4-trifluoromethyl-1,2-dihydroquinolin-6-ylmethyl)benzenesulfonamide;
N,N-Dibenzyl4-(2-oxo-4-trifluoromethyl-1,2-dihydroquinolin-6-ylmethyl)benzenesulfonamide;
N,N-Bis(2-methoxyethyl)4-(2-oxo-4-trifluoromethyl-1,2-dihydroquinolin-6-ylmethyl)benzenesulfonamide;
N-Methyl4-(2-oxo-4-trifluoromethyl-1,2-dihydroquinolin-6-ylmethyl)-N-(2-pyridin-2-ylethyl)benzenesulfonamide;
N-Methyl-4-(2-oxo-4-trifluoromethyl-1,2-dihydroquinolin-6-ylmethyl)-N-phenethylbenzenesulfonamide;
N-(4-Ethynylphenyl)-4-(2-oxo-4-trifluoromethyl-1,2-dihydroquinolin-6-ylmethyl)benzenesulfonamide;
N-(3-Cyanophenyl)4-(2-oxo-4-trifluoromethyl-1,2-dihydroquinolin-6-ylmethyl)-benzenesulfonamide;
N-(3-Ethylphenyl)4-(2-oxo-4-trifluoromethyl-1,2-dihydroquinolin-6-ylmethyl)benzenesulfonamide;
N-(2-Chlorophenyl)-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-quinolin-6-ylbenzenesulfonamide;
N-Indan-5-yl-4-(2-oxo-4-trifluoromethyl-1,2-dihydroquinolin-6-ylmethyl)-benzenesulfonamide;
N-(3-Acetylphenyl)-4-(2-oxo-4-trifluoromethyl-1,2-dihydroquinolin-6-ylmethyl)benzenesulfonamide;
N-(4-Methylbiphenyl-3-yl)-4-(2-oxo-4-trifluoromethyl-1,2-dihydroquinolin-6-ylmethyl)-benzenesulfonamide;
N-[3-(1-Hydroxyethyl)phenyl]-4-(2-oxo-4-trifluoromethyl-1,2-dihydroquinolin-6-ylmethyl)-benzenesulfonamide;
N-(3-Methylsulfanylphenyl)4-(2-oxo-4-trifluoromethyl-1,2-dihydroquinolin-6-ylmethyl)-benzenesulfonamide;
N-(5-Fluoro-2-methylphenyl)-4-(2-oxo-4-trifluoromethyl-1,2-dihydroquinolin-6-ylmethyl)-benzenesulfonamide;

N-(4-Chlorophenyl)-4-(2-oxo-4-trifluoromethyl-1,2-dihydroquinolin-6-ylmethyl)-benzenesulfonamide;
N-Isoquinolin-3-yl-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-quinolin-3-ylbenzenesulfonamide;
4-(2-Oxo-4-trifluoromethyl-1,2-dihydroquinolin-6-ylmethyl)-N-quinolin-5-ylbenzenesulfonamide;
4-(2-Oxo-4-trifluoromethyl-1,2-dihydroquinolin-6-ylmethyl)-N-quinolin-8-ylbenzenesulfonamide;
N-Isoquinolin-5-yl4-(2-oxo-4-trifluoromethyl-1,2-dihydroquinolin-6-ylmethyl)-benzenesulfonamide;
N-(4-Cyano-5-methylsulfanyl-2H-pyrazol-3-yl)-4-(2-oxo-4-trifluoromethyl-1,2-dihydroquinolin-6-ylmethyl)-benzenesulfonamide;
N-(2,5-Dimethoxyphenyl)4-(2-oxo-4-trifluoromethyl-1,2-dihydroquinolin-6-ylmethyl)-benzenesulfonamide;
N-(3,5-Dimethoxyphenyl)-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(3,4,5-trifluorophenyl)-benzenesulfonamide;
N-(3-Difluoromethoxyphenyl)4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(5-phenyl-2H-pyrazol-3-yl)-benzenesulfonamide;
N-(3-Oxazol-5-ylphenyl)-4-(2-oxo-4-trifluoromethyl-1,2-dihydroquinolin-6-ylmethyl)benzenesulfonamide;
4-(2-Oxo-4-trifluoromethyl-1,2-dihydroquinolin-6-ylmethyl)-N-(3-trifluoromethylphenyl)-benzenesulfonamide;
N-(2-Bromophenyl)4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(2-piperidin-1-ylphenyl)-benzenesulfonamide;
4-(2-Oxo-4-trifluoromethyl-1,2-dihydroquinolin-6-ylmethyl)-N-(3-trifluoromethoxyphenyl)-benzenesulfonamide;
N-(3-Benzylphenyl)4-(2-oxo-4-trifluoromethyl-1,2-dihydroquinolin-6-ylmethyl)-benzenesulfonamide;
N-(3-Benzyloxyphenyl)-4-(2-oxo-4-trifluoromethyl-1,2-dihydroquinolin-6-ylmethyl)-benzenesulfonamide;
N-Benzyl-N-(4-methoxyphenyl)4-(2-oxo-4-trifluoromethyl-1,2-dihydroquinolin-6-ylmethyl)-benzenesulfonamide;
N-{2-[(Cyclohexylmethyl-amino)methyl]phenyl}-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(2,2,3,3-tetrafluoro-2,3-dihydrobenzo[1,4]dioxin-5-yl)-benzenesulfonamide;
N-[4-(Isopropylphenylamino)-phenyl]-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-[4-(3-trifluoromethylpyrazol-1-yl)phenyl]-benzenesulfonamide;
N-(3-Methoxyphenyl)-4-(2-oxo-4-trifluoromethyl-1,2-dihydroquinolin-6-ylmethyl)-benzenesulfonamide;
N-(2-Hydroxyethyl)-4-(2-oxo-4-trifluoromethyl-1,2-dihydroquinolin-6-ylmethyl)-benzenesulfonamide;
N-(1-Benzylpiperidin-4-yl)-4-(2-oxo-4-trifluoromethyl-1,2-dihydroquinolin-6-ylmethyl)-benzenesulfonamide;
N-(2-Methoxyethyl)-4-(2-oxo-4-trifluoromethyl-1,2-dihydroquinolin-6-ylmethyl)-benzenesulfonamide;
N-(3,3-Dimethylbutyl)-4-(2-oxo-4-trifluoromethyl-1,2-dihydroquinolin-6-ylmethyl)-benzenesulfonamide;
N-(5-Methylfuran-2-ylmethyl)4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(2-pyrrolidin-1-yl-ethyl)-benzenesulfonamide;
4-(2-Oxo-4-trifluoromethyl-1,2-dihydroquinolin-6-ylmethyl)-N-phenethylbenzenesulfonamide;
N-(3-Methylbenzyl)-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(2-pyridin-2-ylethyl)-benzenesulfonamide;
N-(3-Imidazol-1-ylpropyl)-4-(2-oxo-4-trifluoromethyl-1,2-dihydroquinolin-6-ylmethyl)-benzenesulfonamide;
N-(2-Cyclohex-1-enylethyl)-4-(2-oxo-4-trifluoromethyl-1,2-dihydroquinolin-6-ylmethyl)-benzenesulfonamide;
N-(2-Morpholin-4-ylethyl)-4-(2-oxo-4-trifluoromethyl-1,2-dihydroquinolin-6-ylmethyl)-benzenesulfonamide;
N-(3-Dimethylamino-2,2-dimethylpropyl)-4-(2-oxo-4-trifluoromethyl-1,2-dihydroquinolin-6-ylmethyl)-benzenesulfonamide;
N-(1-Methyl-1-phenylethyl)-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(2-phenylpropyl)-benzenesulfonamide;
N-(3-Methoxybenzyl)-4-(2-oxo-4-trifluoromethyl-1,2-dihydroquinolin-6-ylmethyl)-benzenesulfonamide;
N-(5-Fluoro-2-methylbenzyl)-4-(2-oxo-4-trifluoromethyl-1,2-dihydroquinolin-6-ylmethyl)-benzenesulfonamide;
N-[3-(2-Oxopyrrolidin-1-yl)propyl]-4-(2-oxo-4-trifluoromethyl-1,2-dihydroquinolin-6-ylmethyl)-benzenesulfonamide;
N-(2,6-Difluorobenzyl)-4-(2-oxo-4-trifluoromethyl-1,2-dihydroquinolin-6-ylmethyl)-benzenesulfonamide;
4-(2-Oxo-4-trifluoromethyl-1,2-dihydroquinolin-6-ylmethyl)-N-(4-phenylbutyl)-benzenesulfonamide;
N-(2-Ethoxybenzyl)-4-(2-oxo-4-trifluoromethyl-1,2-dihydroquinolin-6-ylmethyl)-benzenesulfonamide;
N-(3-Hydroxy-1-phenylpropyl)4-(2-oxo-4-trifluoromethyl-1,2-dihydroquinolin-6-ylmethyl)-benzenesulfonamide;
N-(2-Methylsulfanylbenzyl)-4-(2-oxo-4-trifluoromethyl-1,2-dihydroquinolin-6-ylmethyl)-benzenesulfonamide;
N-[2-(4-Chlorophenyl)ethyl]-4-(2-oxo-4-trifluoromethyl-1,2-dihydroquinolin-6-ylmethyl)-benzenesulfonamide;
N-[3-(4-Methylpiperazin-1-yl)propyl]-4-(2-oxo-4-trifluoromethyl-1,2-dihydroquinolin-6-ylmethyl)-benzenesulfonamide;
N-(5-Chloro-2-fluorobenzyl)-4-(2-oxo-4-trifluoromethyl-1,2-dihydroquinolin-6-ylmethyl)-benzenesulfonamide;
N-(3-Chloro-2-fluorobenzyl)-4-(2-oxo-4-trifluoromethyl-1,2-dihydroquinolin-6-ylmethyl)-benzenesulfonamide;
N-(2-Chloro-6-fluorobenzyl)-4-(2-oxo-4-trifluoromethyl-1,2-dihydroquinolin-6-ylmethyl)-benzenesulfonamide;
N-[2-(1H-Indol-3-yl)ethyl]-4-(2-oxo-4-trifluoromethyl-1,2-dihydroquinolin-6-ylmethyl)-benzenesulfonamide;
N-(3,5-Dimethoxybenzyl)-4-(2-oxo-4-trifluoromethyl-1,2-dihydroquinolin-6-ylmethyl)-benzenesulfonamide;
N-[2-(4-Fluorophenyl)-1,1-dimethylethyl]-4-(2-oxo-4-trifluoromethyl-1,2-dihydroquinolin-6-ylmethyl)-benzenesulfonamide;

N-(2-tert-Butylsulfanylethyl)-4-(2-oxo-4-trifluoromethyl-1,2-dihydroquinolin-6-ylmethyl)-benzenesulfonamide;
N-(2-Difluoromethoxybenzyl)-4-(2-oxo-4-trifluoromethyl-1,2-dihydroquinolin-6-ylmethyl)-benzenesulfonamide;
N-(2-Chloro-6-fluoro-3-methylbenzyl)-4-(2-oxo-4-trifluoromethyl-1,2-dihydroquinolin-6-ylmethyl)-benzenesulfonamide;
N-(2,4-Dichlorobenzyl)-4-(2-oxo-4-trifluoromethyl-1,2-dihydroquinolin-6-ylmethyl)-benzenesulfonamide;
N-(1-Benzylpyrrolidin-3-yl)4-(2-oxo-4-trifluoromethyl-1,2-dihydroquinolin-6-ylmethyl)-benzenesulfonamide;
N-(2-Chloro-3,6-difluorobenzyl)-4-(2-oxo-4-trifluoromethyl-1,2-dihydroquinolin-6-ylmethyl)-benzenesulfonamide;
N-(3-Hydroxymethyl-bicyclo[2.2.1]hept-2-yl)4-(2-oxo-4-trifluoromethyl-1,2-dihydroquinolin-6-ylmethyl)-benzenesulfonamide;
[4-(2-Oxo-4-trifluoromethyl-1,2-dihydroquinolin-6-ylmethyl)-benzenesulfonylamino]-phenylacetic acid ethyl ester;
N-(2-Fluoro-5-trifluoromethylbenzyl)-4-(2-oxo-4-trifluoromethyl-1,2-dihydroquinolin-6-ylmethyl)-benzenesulfonamide;
3-[4-(2-Oxo-4-trifluoromethyl-1,2-dihydroquinolin-6-ylmethyl)-benzenesulfonylamino]-3-phenylpropionic acid ethyl ester;
N-(2,2-Diphenylethyl)-4-(2-oxo-4-trifluoromethyl-1,2-dihydroquinolin-6-ylmethyl)-benzenesulfonamide;
N-(2-Benzyloxycyclohexyl)-4-(2-oxo-4-trifluoromethyl-1,2-dihydroquinolin-6-ylmethyl)-benzenesulfonamide;
N-[2-(2-Hydroxymethyl-phenylsulfanyl)benzyl]4-(2-oxo-4-trifluoromethyl-1,2-dihydroquinolin-6-ylmethyl)-benzenesulfonamide;
N-Cyclohexyl-N-(2-hydroxyethyl)-4-(2-oxo-4-trifluoromethyl-2H-chromen-6-ylmethyl)benzenesulfonamide;
N-Methyl-N-(1-methylpiperidin-4-yl)-4-(2-oxo-4-trifluoromethyl-2H-chromen-6-ylmethyl)-benzenesulfonamide;
N,N-Dibutyl-4-(2-oxo-4-trifluoromethyl-2H-chromen-6-ylmethyl)benzenesulfonamide;
N-Ethyl-4-(2-oxo-4-trifluoromethyl-2H-chromen-6-ylmethyl)-N-pyridin4-ylmethyl-benzenesulfonamide;
N-Butyl-N-ethyl-4-(2-oxo-4-trifluoromethyl-2H-chromen-6-ylmethyl)benzenesulfonamide;
N-Butyl-N-(2-hydroxyethyl)-4-(2-oxo-4-trifluoromethyl-2H-chromen-6-ylmethyl)-benzenesulfonamide;
N-Isopropyl-N-methyl4-(2-oxo-4-trifluoromethyl-2H-chromen-6-ylmethyl)-benzenesulfonamide;
N-(2-Hydroxyethyl)-4-(2-oxo-4-trifluoromethyl-2H-chromen-6-ylmethyl)-N-propylbenzenesulfonamide;
N-Benzyl-N-(2-hydroxyethyl)-4-(2-oxo-4-trifluoromethyl-2H-chromen-6-ylmethyl)-benzenesulfonamide;
N-Cyclopropylmethyl4-(2-oxo-4-trifluoromethyl-2H-chromen-6-ylmethyl)-N-propylbenzenesulfonamide;
N-(2-Hydroxyethyl)-4-(2-oxo-4-trifluoromethyl-2H-chromen-6-ylmethyl)-N-pentylbenzenesulfonamide;
N-Cyclohexyl-N-methyl-4-(2-oxo-4-trifluoromethyl-2H-chromen-6-ylmethyl)-benzenesulfonamide;
N-Butyl-N-methyl-4-(2-oxo-4-trifluoromethyl-2H-chromen-6-ylmethyl)benzenesulfonamide;
N-(2-Cyanoethyl)-N-methyl-4-(2-oxo-4-trifluoromethyl-2H-chromen-6-ylmethyl)-benzenesulfonamide;
N,N-Dibenzyl-4-(2-oxo-4-trifluoromethyl-2H-chromen-6-ylmethyl)benzenesulfonamide;
N-Benzyl-N-ethyl-4-(2-oxo-4-trifluoromethyl-2H-chromen-6-ylmethyl)benzenesulfonamide;
N-Methyl4-(2-oxo-4-trifluoromethyl-2H-chromen-6-ylmethyl)-N-(2-pyridin-2-ylethyl)benzenesulfonamide;
N-Methyl-4-(2-oxo-4-trifluoromethyl-2H-chromen-6-ylmethyl)-N-phenethyl-benzenesulfonamide;
4-(2-Oxo-4-trifluoromethyl-2H-chromen-6-ylmethyl)-N-phenylbenzenesulfonamide;
N-Methyl-4-(2-oxo-4-trifluoromethyl-2H-chromen-6-ylmethyl)-N-phenylbenzenesulfonamide;
4-(2-Oxo-4-trifluoromethyl-2H-chromen-6-ylmethyl)-N-m-tolylbenzenesulfonamide;
4-(2-Oxo-4-trifluoromethyl-2H-chromen-6-ylmethyl)-N-p-tolylbenzenesulfonamide;
N-(4-Fluorophenyl)-4-(2-oxo-4-trifluoromethyl-2H-chromen-6-ylmethyl)benzenesulfonamide
N-(4-Ethynylphenyl)-4-(2-oxo-4-trifluoromethyl-2H-chromen-6-ylmethyl)-benzenesulfonamide;
N-(3-Ethylphenyl)-4-(2-oxo-4-trifluoromethyl-2H-chromen-6-ylmethyl)-benzenesulfonamide;
N-(4-Ethylphenyl)-4-(2-oxo-4-trifluoromethyl-2H-chromen-6-ylmethyl)-benzenesulfonamide;
N-(2-Hydroxymethylphenyl)-4-(2-oxo-4-trifluoromethyl-2H-chromen-6-ylmethyl)-benzenesulfonamide;
N-(3-Hydroxymethylphenyl)-4-(2-oxo-4-trifluoromethyl-2H-chromen-6-ylmethyl)-benzenesulfonamide;
N-(2-Methoxyphenyl)-4-(2-oxo-4-trifluoromethyl-2H-chromen-6-ylmethyl)-benzenesulfonamide;
N-(4-Hydroxymethylphenyl)-4-(2-oxo-4-trifluoromethyl-2H-chromen-6-ylmethyl)-benzenesulfonamide;
4-(2-Oxo-4-trifluoromethyl-2H-chromen-6-ylmethyl)-N-quinolin-6-ylbenzenesulfonamide;
N-(4-Cyanomethylphenyl)-4-(2-oxo-4-trifluoromethyl-2H-chromen-6-ylmethyl)-benzenesulfonamide;
N-Indan-5-yl4-(2-oxo-4-trifluoromethyl-2H-chromen-6-ylmethyl)benzenesulfonamide;
N-Indan-4-yl-4-(2-oxo-4-trifluoromethyl-2H-chromen-6-ylmethyl)benzenesulfonamide;
N-(3-Acetylphenyl)-4-(2-oxo-4-trifluoromethyl-2H-chromen-6-ylmethyl)benzenesulfonamide;
N-(4-Isopropylphenyl)-4-(2-oxo-4-trifluoromethyl-2H-chromen-6-ylmethyl)-benzenesulfonamide;
N-Benzo[1,3]dioxol-5-yl4-(2-oxo-4-trifluoromethyl-2H-chromen-6-ylmethyl)-benzenesulfonamide;
N-(4-Methylbiphenyl-3-yl)-4-(2-oxo-4-trifluoromethyl-2H-chromen-6-ylmethyl)-benzenesulfonamide;
N-[3-(1-Hydroxyethyl)phenyl]4-(2-oxo-4-trifluoromethyl-2H-chromen-6-ylmethyl)-benzenesulfonamide;
N-(3-Methylsulfanylphenyl)-4-(2-oxo-4-trifluoromethyl-2H-chromen-6-ylmethyl)-benzenesulfonamide;
N-(4-Chlorophenyl)-4-(2-oxo-4-trifluoromethyl-2H-chromen-6-ylmethyl)benzenesulfonamide;
N-Isoquinolin-3-yl-4-(2-oxo-4-trifluoromethyl-2H-chromen-6-ylmethyl)benzenesulfonamide;
4-(2-Oxo-4-trifluoromethyl-2H-chromen-6-ylmethyl)-N-quinolin-8-ylbenzenesulfonamide;
N-(4-Cyano-5-methylsulfanyl-2H-pyrazol-3-yl)4-(2-oxo-4-trifluoromethyl-2H-chromen-6-ylmethyl)benzenesulfonamide;
N-(2-Methylquinolin-6-yl)4-(2-oxo-4-trifluoromethyl-2H-chromen-6-ylmethyl)-benzenesulfonamide;
N-(2,5-Dimethoxyphenyl)-4-(2-oxo-4-trifluoromethyl-2H-chromen-6-ylmethyl)-benzenesulfonamide;
N-(3,5-Dimethoxyphenyl)-4-(2-oxo-4-trifluoromethyl-2H-chromen-6-ylmethyl)-benzenesulfonamide;
N-(3-Isopropoxyphenyl)-4-(2-oxo-4-trifluoromethyl-2H-chromen-6-ylmethyl)-benzenesulfonamide;

N-(3-Difluoromethoxyphenyl)-4-(2-oxo-4-trifluoromethyl-2H-chromen-6-ylmethyl)-benzenesulfonamide;
N-(3-Oxazol-5-ylphenyl)-4-(2-oxo-4-trifluoromethyl-2H-chromen-6-ylmethyl)-benzenesulfonamide;
4-(2-Oxo-4-trifluoromethyl-2H-chromen-6-ylmethyl)-N-(3-trifluoromethylphenyl)-benzenesulfonamide;
4-(2-Oxo-4-trifluoromethyl-2H-chromen-6-ylmethyl)-N-(2-piperidin-1-ylphenyl)-benzenesulfonamide;
4-(2-Oxo-4-trifluoromethyl-2H-chromen-6-ylmethyl)-N-(3-trifluoromethoxyphenyl)-benzenesulfonamide;
{4-[4-(2-Oxo-4-trifluoromethyl-2H-chromen-6-ylmethyl)-benzenesulfonylamino]-phenyl}acetic acid ethyl ester;
N-(3-Benzylphenyl)-4-(2-oxo-4-trifluoromethyl-2H-chromen-6-ylmethyl)benzenesulfonamide;
N-(4-Ethoxyphenyl)-4-(2-oxo-4-trifluoromethyl-2H-chromen-6-ylmethyl)-benzenesulfonamide;
N-[4-(2-Hydroxyethyl)phenyl]4-(2-oxo-4-trifluoromethyl-2H-chromen-6-ylmethyl)-benzenesulfonamide;
N-(3-Benzyloxyphenyl)-4-(2-oxo-4-trifluoromethyl-2H-chromen-6-ylmethyl)-benzenesulfonamide;
N-(3,5-Di-tert-butylphenyl)-4-(2-oxo-4-trifluoromethyl-2H-chromen-6-ylmethyl)-benzenesulfonamide;
N-Benzyl-N-(4-methoxyphenyl)-4-(2-oxo-4-trifluoromethyl-2H-chromen-6-ylmethyl)benzenesulfonamide;
4-(2-Oxo-4-trifluoromethyl-2H-chromen-6-ylmethyl)-N-[4-(3-trifluoromethylpyrazol-1-yl)phenyl]benzenesulfonamide;
N-(3-Methoxyphenyl)-4-(2-oxo-4-trifluoromethyl-2H-chromen-6-ylmethyl)benzene-sulfonamide;
N-(1-Benzylpiperidin-4-yl)4-(2-oxo-4-trifluoromethyl-2H-chromen-6-ylmethyl)benzenesulfonamide;
N-Cyclopentyl-4-(2-oxo-4-trifluoromethyl-2H-chromen-6-ylmethyl)benzenesulfonamide;
N-(3-Methylbutyl)-4-(2-oxo-4-trifluoromethyl-2H-chromen-6-ylmethyl)benzenesulfonamide;
N-(2,3-Dihydroxypropyl)-4-(2-oxo-4-trifluoromethyl-2H-chromen-6-ylmethyl)benzenesulfonamide;
N-(3,3-Dimethylbutyl)-4-(2-oxo-4-trifluoromethyl-2H-chromen-6-ylmethyl)benzenesulfonamide;
N-Benzyl-4-(2-oxo-4-trifluoromethyl-2H-chromen-6-ylmethyl)benzenesulfonamide;
4-(2-Oxo-4-trifluoromethyl-2H-chromen-6-ylmethyl)-N-pyridin-3-ylmethylbenzenesulfonamide;
N-(5-Methylfuran-2-ylmethyl)4-(2-oxo-4-trifluoromethyl-2H-chromen-6-ylmethyl)benzenesulfonamide;
N-Cyclohexylmethyl-4-(2-oxo-4-trifluoromethyl-2H-chromen-6-ylmethyl)benzene-sulfonamide;
N-Cycloheptyl4-(2-oxo-4-trifluoromethyl-2H-chromen-6-ylmethyl)benzenesulfonamide;
N-(1-Hydroxymethyl-cyclopentyl)-4-(2-oxo-4-trifluoromethyl-2H-chromen-6-ylmethyl)benzenesulfonamide;
4-(2-Oxo-4-trifluoromethyl-2H-chromen-6-ylmethyl)-N-phenethylbenzenesulfonamide;
N-(3-Methylbenzyl)-4-(2-oxo-4-trifluoromethyl-2H-chromen-6-ylmethyl)benzenesulfonamide;
N-(4-Methylbenzyl)-4-(2-oxo-4-trifluoromethyl-2H-chromen-6-ylmethyl)benzenesulfonamide;
N-(2-Methylbenzyl)-4-(2-oxo-4-trifluoromethyl-2H-chromen-6-ylmethyl)benzenesulfonamide;
4-(2-Oxo-4-trifluoromethyl-2H-chromen-6-ylmethyl)-N-(1-phenylethyl)-benzenesulfonamide;
N-(4-Fluorobenzyl)-4-(2-oxo-4-trifluoromethyl-2H-chromen-6-ylmethyl)benzenesulfonamide;
N-(3-Imidazol-1-ylpropyl)-4-(2-oxo-4-trifluoromethyl-2H-chromen-6-ylmethyl)benzenesulfonamide;
N-(2-Cyclohex-1-enylethyl)4-(2-oxo-4-trifluoromethyl-2H-chromen-6-ylmethyl)benzenesulfonamide;
4-(2-Oxo-4-trifluoromethyl-2H-chromen-6-ylmethyl)-N-(2-thiophen-2-ylethyl)benzenesulfonamide;
N-(2-Hydroxycyclohexylmethyl)-4-(2-oxo-4-trifluoromethyl-2H-chromen-6-ylmethyl)benzenesulfonamide;
N-Indan-1-yl-4-(2-oxo-4-trifluoromethyl-2H-chromen-6-ylmethyl)benzenesulfonamide;
N-(1-Methyl-1-phenylethyl)-4-(2-oxo-4-trifluoromethyl-2H-chromen-6-ylmethyl)benzenesulfonamide;
4-(2-Oxo-4-trifluoromethyl-2H-chromen-6-ylmethyl)-N-(2-phenylpropyl)-benzenesulfonamide;
4-(2-Oxo-4-trifluoromethyl-2H-chromen-6-ylmethyl)-N-(2-phenoxyethyl)-benzenesulfonamide;
N-(4-Methoxybenzyl)-4-(2-oxo-4-trifluoromethyl-2H-chromen-6-ylmethyl)-benzenesulfonamide;
N-(3-Methoxybenzyl)-4-(2-oxo-4-trifluoromethyl-2H-chromen-6-ylmethyl)-benzenesulfonamide;
N-(2-Hydroxy-1-phenylethyl)-4-(2-oxo-4-trifluoromethyl-2H-chromen-6-ylmethyl)-benzenesulfonamide;
N-(5-Fluoro-2-methylbenzyl)-4-(2-oxo-4-trifluoromethyl-2H-chromen-6-ylmethyl)-benzenesulfonamide;
N-(3-Chlorobenzyl)-4-(2-oxo-4-trifluoromethyl-2H-chromen-6-ylmethyl)benzenesulfonamide;
N-[3-(2-Oxopyrrolidin-1-yl)propyl]4-(2-oxo-4-trifluoromethyl-2H-chromen-6-ylmethyl)benzenesulfonamide;
N-(2,6-Difluorobenzyl)-4-(2-oxo-4-trifluoromethyl-2H-chromen-6-ylmethyl)benzenesulfonamide;
N-(2,3-Dihydrobenzofuran-5-ylmethyl)-4-(2-oxo-4-trifluoromethyl-2H-chromen-6-ylmethyl)benzenesulfonamide;
N-[2-(2-Methoxyphenyl)ethyl]-4-(2-oxo-4-trifluoromethyl-2H-chromen-6-ylmethyl)benzenesulfonamide;
N-(2-Ethoxybenzyl)-4-(2-oxo-4-trifluoromethyl-2H-chromen-6-ylmethyl)benzene-sulfonamide;
N-(3-Hydroxy-1-phenylpropyl)-4-(2-oxo-4-trifluoromethyl-2H-chromen-6-ylmethyl)benzenesulfonamide;
N-(4-Hydroxycyclohexyl)-4-(2-oxo-4-trifluoromethyl-2H-chromen-6-ylmethyl)benzenesulfonamide;
N-(2-Methylsulfanylbenzyl)-4-(2-oxo-4-trifluoromethyl-2H-chromen-6-ylmethyl)benzenesulfonamide;
N-[2-(4-Chlorophenyl)ethyl]-4-(2-oxo-4-trifluoromethyl-2H-chromen-6-ylmethyl)benzenesulfonamide;
N-(2-Chloro-6-methylbenzyl)-4-(2-oxo-4-trifluoromethyl-2H-chromen-6-ylmethyl)benzenesulfonamide;
N-(2,3-Difluoro-4-methylbenzyl)-4-(2-oxo-4-trifluoromethyl-2H-chromen-6-ylmethyl)benzenesulfonamide;
N-(2-Chloro4-fluorobenzyl)-4-(2-oxo-4-trifluoromethyl-2H-chromen-6-ylmethyl)benzenesulfonamide;
N-(2-Difluoromethoxybenzyl)-4-(2-oxo-4-trifluoromethyl-2H-chromen-6-ylmethyl)benzenesulfonamide;
N-(2-Chloro-6-fluoro-3-methylbenzyl)-4-(2-oxo-4-trifluoromethyl-2H-chromen-6-ylmethyl)benzenesulfonamide;
4-(2-Oxo-4-trifluoromethyl-2H-chromen-6-ylmethyl)-N-(2-trifluoromethylbenzyl)-benzenesulfonamide;
N-(2-Chloro-3,6-difluorobenzyl)-4-(2-oxo-4-trifluoromethyl-2H-chromen-6-ylmethyl)benzenesulfonamide;
N-(2-Bromobenzyl)-4-(2-oxo-4-trifluoromethyl-2H-chromen-6-ylmethyl)benzenesulfonamide;
N-(2-Fluoro-5-trifluoromethylbenzyl)-4-(2-oxo-4-trifluoromethyl-2H-chromen-6-ylmethyl)benzene-sulfonamide;
3-[4-(2-Oxo-4-trifluoromethyl-2H-chromen-6-ylmethyl)-benzenesulfonylamino]-3-phenylpropionic acid ethyl ester;

N-(2,2-Diphenylethyl)-4-(2-oxo-4-trifluoromethyl-2H-chromen-6-ylmethyl)benzene-sulfonamide;

N-(4-Bromo-2-fluorobenzyl)-4-(2-oxo-4-trifluoromethyl-2H-chromen-6-ylmethyl)benzenesulfonamide;

N-(2-Benzyloxycyclohexyl)-4-(2-oxo-4-trifluoromethyl-2H-chromen-6-ylmethyl)benzenesulfonamide; and N-[2-(2-Chloro-6-fluorobenzylsulfanyl)ethyl]-4-(2-oxo-4-trifluoromethyl-2H-chromen-6-ylmethyl)benzene-sulfonamide.

7. The compound according to claim 2 in the sulfonamide function is located at the para-position of the benzyl ring.

8. The compound according to claim 7 in which A is $C^1$–$C_6$alkyl$R^6$ and B is hydrogen or $C_1$–$C_6$alkyl.

9. The compound according to claim 7 in which A is hydrogen or $C_1$–$C_6$alkyl$R^6$ and B is optionally substituted cycloalkyl, optionally substituted cycloalkenyl, optionally substituted phenyl, optionally substituted cycloalkylphenyl, optionally substituted heteroaryl or optionally substituted heterocycle.

10. The compound according to claim 7 in which A is hydrogen or $C_1$–$C_6$alkyl, and B is phenyl, which may be optionally substituted.

11. The compound according to claim 7 in which A is optionally substituted phenyl, and B is hydrogen.

* * * * *